(12) United States Patent
Benoit et al.

(10) Patent No.: US 6,814,962 B1
(45) Date of Patent: Nov. 9, 2004

(54) RECOMBINANT VIRUSES AND THEIR USE FOR TREATMENT OF ATHEROSCLEROSIS AND OTHER FORMS OF CORONARY ARTERY DISEASE AND METHOD, REAGENT, AND KIT FOR EVALUATING SUSCEPTIBILITY TO SAME

(75) Inventors: Patrick Benoit, Paris (FR); Patrice Denefle, Saint Maur (FR); Michel Perricaudet, Ecrosnes (FR); M. E. Suzanne Lewis, West Vancouver (CA); Michael R. Hayden, Vancouver (CA)

(73) Assignees: Aventis Pharma S.A., Antony Cedex (FR); The University of British Columbia, Vancouver (CA)

( * ) Notice: Subject to any disclaimer, the term of this patent is extended or adjusted under 35 U.S.C. 154(b) by 0 days.

(21) Appl. No.: 09/713,268

(22) Filed: Nov. 16, 2000

Related U.S. Application Data

(63) Continuation-in-part of application No. 08/817,192, filed as application No. PCT/US95/13620 on Oct. 11, 1995, which is a continuation-in-part of application No. 08/737,954, filed as application No. PCT/FR95/00669 on May 22, 1995, now abandoned, which is a continuation of application No. 08/320,604, filed on Oct. 11, 1994, now Pat. No. 5,658,729.

(30) Foreign Application Priority Data

Jun. 2, 1994 (FR) ............................................. 94 06759

(51) Int. Cl.$^7$ .............................................. A61K 48/00
(52) U.S. Cl. ..................... 424/93.2; 514/44; 435/320.1; 435/91.4; 435/455
(58) Field of Search .......................... 514/44; 424/93.2; 435/320.1, 91.4, 455

(56) References Cited

U.S. PATENT DOCUMENTS

| 5,173,414 A | 12/1992 | Lebkowski et al. |
| 5,521,076 A | 5/1996 | Mulligan et al. |

FOREIGN PATENT DOCUMENTS

| WO | WO 90/09441 | 8/1990 |
| WO | WO 93/00426 | 1/1993 |
| WO | WO 95/27512 | 10/1995 |

OTHER PUBLICATIONS

Gunzburg et al. Virus vector design in gene therapy pp. 410–417 vol. 1, No. 9 1989.*
Rosenberg et al. Gene therapist, heal thyself pp. 1751 vol. 287, 2000.*
Verma et al. Gene therapy promises, problems and prospects pp. 239–242 vol. 389 1997.*
Anderson Human gene therapy vol. 392, 1998 pp. 25–30.*
Liu et al. Phenotypic correction of feline lipoprotein lipase defiency by adenoviral gene transfer pp. 21–32 2000.*
Khurana et al. Gene therapy for cardiovascular disease a case for cautious optimism pp. 1210–1216 2001.*
Stedronsky Interaction of bile acids and cholesterol with non–systemic agents having hypocholesterolemia properties pp. 255–287 1994.*
Beg et al., Lipoprotein lipase Bethesda: A single amino acid substitution (Ala–176—Thr) leads to abnormal heparin binding and loss of enzymic activity, Proc. Natl. Acad. Sci., 87:3474–78 (1990).
Berryman et al., Site–directed Mutagenesis of a Putative Heparin Binding Domain of Avian Lipoprotein Lipase, The Journal of Biological Chemistry, vol. 268, 5:3272–76 (1993).
Braun et al., Biochem J., 287:337–47 (1992).
Coghlan, News Scientist, 148:14–15 (1995).
Crystal, Science, 270:404–09 (1995).
Datta et al., J.. Biol. Chem., vol. 262, 22:10588–93 (1987).
Holm et al., Hormone–sensitive lipase: structure, function, evolution and overproduction in insect cells using the baculovirus expression system, Protein Engineering, 7:537–41 (1990).
Humpries et al., The Molecular Genetics of Pediatric Lipid Disorders: Recent Progress and Future Research Directions, Pediatric Research, vol. 34, 4:403–15 (1993).
Ledley, Human Gene Therapy, 6:1129–44 (1995).
Lewis et al., Human Gene Therapy, 6:853:63 (1995).
Lowe et al., Cloning and Characterization of Human Pancreatic Lipase cDNA, The Journal of Biological Chemistry vol. 264, 33:20042–48 (1989).
Maeda et al., Gene Therapy Strategy for the Pancreatic Insufficiency of Cystic Fibrosis: Adenovirus–Mediated Transfer of the Human Pancreatic Lipase cDNA, Clinical Research 41(2):206A (1993).
Morsy et al., JAMA, vol. 270, 19:2338–45 (1993).
Mastrangelo et al., Seminars in Oncology, vol. 23 1:4–21 (1996).
Semenkovich et al., J. Biol. Chem., vol. 10, 5:5429–33 (1990).
Stratford–Perricaudet et al., Gene transfer into animals: the promise of adenovirus, Human Gene Transfer 291:51–61 (1991).
Thompson et al., P.N.A.S., vol. 86, 20:7928–32 (1995).
Wilson et al., Hepatocyte–directed Gene Transfer in Vivo Leads to Transient Improvement of Hypercholesterolemia in Low Density Lipoprotein Receptor–deficients Rabbits, The Journal of Biological Chemistry, vol. 267, 2:963–67 (1992).

* cited by examiner

*Primary Examiner*—Dave T. Nguyen
(74) *Attorney, Agent, or Firm*—Finnegan, Henderson, Farabow, Garrett & Dunner, L.L.P.

(57) ABSTRACT

Recombinant viruses comprising a heterologous DNA sequence coding for a lipase involved in lipoprotein metabolism. The invention also concerns the preparation and use in therapy of said recombinant viruses, especially for the treatment or prevention of dyslipoproteinemia-related pathologies.

15 Claims, 7 Drawing Sheets

FIG. 3  pXL CMV LPL pXL RSV LPL

SEQUENCE LISTING

<160> NUMBER OF SEQ ID NOS: 9

<210> SEQ ID NO 1
<211> LENGTH: 35
<212> TYPE: DNA
<213> ORGANISM: Homo sapiens

<400> SEQUENCE: 1
ttagatctat cgatagatgg agagcaaagc ccctg                35

<210> SEQ ID NO 2
<211> LENGTH: 30
<212> TYPE: DNA
<213> ORGANISM: Homo sapiens

<400> SEQUENCE: 2
tacattcctg ttaccgtcca gccatggatc                      30

<210> SEQ ID NO 3
<211> LENGTH: 14
<212> TYPE: DNA
<213> ORGANISM: Homo sapiens

<400> SEQUENCE: 3
agctacatcg atgt                                       14

<210> SEQ ID NO 4
<211> LENGTH: 36
<212> TYPE: DNA
<213> ORGANISM: Homo sapiens

<400> SEQUENCE: 4
atcggatcca tcgatgcagc tcctccagag ggacgc                36

<210> SEQ ID NO 5
<211> LENGTH: 36
<212> TYPE: DNA
<213> ORGANISM: Homo sapiens

<400> SEQUENCE: 5

-continued

```
atctctagag tcgacatgcc gttctttgtt ctgtag                          36

<210> SEQ ID NO 6
<211> LENGTH: 15
<212> TYPE: DNA
<213> ORGANISM: Homo sapiens

<400> SEQUENCE: 6
gagatcaata aagtc                                                 15

<210> SEQ ID NO 7
<211> LENGTH: 15
<212> TYPE: DNA
<213> ORGANISM: Homo sapiens

<400> SEQUENCE: 7
gagatcagta aagtc                                                 15

<210> SEQ ID NO 8
<211> LENGTH: 24
<212> TYPE: DNA
<213> ORGANISM: Homo sapiens

<400> SEQUENCE: 8
ctgcttcttt tggctctgac tgta                                       24

<210> SEQ ID NO 9
<211> LENGTH: 24
<212> TYPE: DNA
<213> ORGANISM: Homo sapiens

<400> SEQUENCE: 9
ctgcttcttt tggctctgac tgta                                       24
```

RECOMBINANT VIRUSES AND THEIR USE FOR TREATMENT OF ATHEROSCLEROSIS AND OTHER FORMS OF CORONARY ARTERY DISEASE AND METHOD, REAGENT, AND KIT FOR EVALUATING SUSCEPTIBILITY TO SAME

This application is a continuation-in-part of application Ser. No. 08/737,954, filed Dec. 16, 1996, abandoned, which is a 371 of international application PCT/FR95/00669, filed May 22, 1995, and a continuation-in-part of application Ser. No. 08/817,192, filed Apr. 11, 1997, which is a 371 of international application PCT/US95/13620, filed Oct. 11, 1995, which is a continuation of application Ser. No. 08/320,604, filed Oct. 11, 1994, issued as U.S. Pat. No. 5,658,729, each of which is incorporated by reference herein.

The present invention relates to recombinant vectors of viral origin, to their preparation and to their use, in particular for the treatment and/or prevention of pathologies associated with dyslipoproteinaemias. More particularly, it relates to recombinant viruses containing a DNA sequence coding for a lipase involved in lipoprotein metabolism. The invention also relates to the preparation of these viral vectors, to pharmaceutical compositions containing them and to their therapeutic use, in particular, in gene therapy by which lipoprotein deficiencies can be treated. In addition, the invention relates to a method, reagent and kit for evaluating susceptibility to and causation of premature atherosclerosis and other forms of coronary artery disease.

BACKGROUND OF THE INVENTION

Dyslipoproteinaemias are disorders of the metabolism of the lipoproteins responsible for transport of lipids such as cholesterol and triglycerides in the blood and the peripheral fluids. They lead to major pathologies associated, respectively, with hypercholesterolaemia or hypertriglyceridaemia, such as, for example, coronary artery disease.

"Coronary artery disease" is a collective term for a variety of symptomatic conditions including angina, myocardial infarction, and non-specific chest, arm and face pain, which result from atherosclerosis of the arteries that supply blood to the heart.

"Premature atherosclerosis" as used herein refers to the clinical presentation of signs and symptoms of coronary artery disease before the age of 65.

Atherosclerosis, commonly known as "hardening of the arteries," is a complex disease of polygenic origin, which is defined from a histological standpoint by deposits (lipid or fibrolipid plaques) of lipids and of other blood derivatives within the wall or endothelium of the large arteries (aorta, coronary arteries, carotid). These plaques, which are more or less calcified according to the degree of progression of the process, may be coupled with lesions, and are associated with the accumulation of fatty deposits in the arteries, consisting essentially of cholesterol esters.

The plaques are accompanied by a thickening of the arterial wall, with hypertrophy of the smooth muscle, appearance of foam cells and accumulation of fibrous tissue. The atheromatous plaque protrudes markedly from the wall, endowing it with a stenosing character responsible for vascular occlusions by atheroma, thrombosis or embolism which occur in those patients who are most affected. Thus, the dyslipoproteinaemias can lead to very serious cardiovascular pathologies such as infarction, sudden death, cardiac decompensation, stroke, and the like.

Because of the significant relationship between coronary artery disease and heart attacks, considerable effort has been devoted to identifying the biochemical causes of atherosclerosis. This research has shown that high levels of total cholesterol, low density lipoprotein (LDL), very low density lipoprotein (VLDL) and triglycerides are associated with increased risk of coronary artery disease, while high levels of high density lipoproteins (HDL) are associated with decreased risk of coronary artery disease. See, Gordon et al., *The Amer. J. Med.* 62: 707–714 (1977). However, while observation of lipoproteins, cholesterol and triglycerides can provide a basis for identifying individuals at risk of coronary artery disease, the levels of these substances are themselves symptoms of an underlying biochemical defect which remains unidentified. Thus, specific treatment of the ultimate cause rather than an intermediate condition, and prediction of risk prior to the onset of this intermediate condition is not possible through such observation.

Studies directed towards the underlying cause of coronary artery disease have identified a number of mutations in genes coding for proteins involved in lipid transport and metabolism that appear to be associated with an increased risk. Examples include a large number of mutations in the low-density lipoprotein receptor gene, Hobbs et al., *Human Mutations* 1: 445–466 (1992), and a single mutation in the apolipoprotein-B (Apo-B) gene which underlies familial defective Apo-B in many parts of the world. Soria et al., *Proc. Nat'l Acad Sci. USA* 86: 587–91 (1989). In addition, mutations in other genes which play a significant role in HDL metabolism 20 such as the cholesterol ester transferase protein (CETP) gene, Brown et al., *Nature* 342: 448–451 (1989) and the gene for Apo-Al, Rubin et al., *Nature* 353: 265–266 (1991), have also been shown to be associated with either enhanced resistance or increased susceptibility to atherosclerosis. However, these mutations are uncommon and thus far no specific mutation in any gene has been found in a significant number (i.e., >1%) of patients with coronary artery disease or premature atherosclerosis. Accordingly, these test results while interesting do not offer the opportunity to provide evaluation or therapy to significant numbers of patients At the present time these pathologies, and especially the hypercholesterolaemias, are treated essentially by means of compounds which act either on cholesterol biosynthesis (hydroxymethylglutarylcoenzyme A reductase inhibitors, statins), or on the uptake and removal of biliary cholesterol (sequestering agents or resins), or alternatively on lipolysis by a mode of action which remains to be elucidated at molecular level (fibrates). Consequently, all the major classes of medicinal products which have been used in this indication (sequestering agents, fibrates or statins) are directed only towards the preventive aspect of atheromatous plaque formation and not, in fact, towards the treatment of atheroma. Current treatments of atheroma following coronary accident are merely palliative, since they do not intervene in cholesterol homeostasis and are surgical procedures (coronary bypass, angioplasty).

SUMMARY OF THE INVENTION

It has now been found that a single point mutation in the human lipoprotein lipase gene which results in an A→G nucleotide change at codon 291 (nucleotide 1127) of the lipoprotein lipase gene, and a substitution of serine for the normal asparagine in the lipoprotein lipase gene product is seen with increased frequency in patients with coronary artery disease, and is associated with an increased susceptibility to coronary artery disease, including in particular premature atherosclerosis. This is expressed as a diminished catalytic activity of lipoprotein lipase, lower HDL-cholesterol levels and higher triglyceride levels. Thus, in accordance with one embodiment of the present invention there is provided a method for evaluating susceptibility of a human individual to premature atherosclerosis and other forms of coronary artery disease comprising the steps of:

(a) obtaining a sample of DNA from the individual; and
(b) evaluating the sample of DNA for the presence of nucleotides encoding a serine residue as amino acid 291 of the lipoprotein lipase gene product.

The presence of a serine residue is indicative of increased susceptibility in the patient.

The invention further provides a kit for performing the method of the invention. Such a kit comprises a pair of primers selected to amplify a region of a human lipoprotein lipase gene spanning amino acid 291 of human lipoprotein lipase. Appropriate additional reagents may also be included in the kit such as polymerase enzymes, nucleoside stock solutions and the like.

A further aspect of the present invention is a method of treating patients suffering from or likely to suffer from premature atherosclerosis and other forms of coronary artery disease as a result of a lipoprotein lipase deficiency using gene therapy. This, for example, may be accomplished using adenovirus-mediated or retrovirus-mediated gene therapy, and can be performed using either an in vivo or an ex vivo approach.

Thus, the present invention also constitutes a novel therapeutic approach to the treatment of pathologies associated with dyslipoproteinaemias, which may be caused by, for example, lipoprotein lipase deficiency. It proposes an advantageous solution to the drawbacks of the prior art, by demonstrating the possibility of treating pathologies associated with dyslipoproteinaemias by gene therapy, by the transfer and expression in vivo of a gene coding for a lipase involved in lipoprotein metabolism. The invention thus affords a simple means permitting specific and effective treatment of these pathologies.

Gene therapy consists in correcting a deficiency or an abnormality (mutation, aberrant expression, and the like) or in providing for the expression of a protein of therapeutic interest by introducing genetic information into the affected cell or organ. This genetic information may be introduced either ex vivo into a cell extracted from the organ, the modified cell then being reintroduced into the body, or directly in vivo into the appropriate tissue. In this second case, different techniques exist, including various techniques of transfection involving complexes of DNA and DEAE-dextran (Pagano et al., J. Virol. 1 (1967) 891), of DNA and nuclear proteins (Kaneda et al., Science 243 (1989) 375), and of DNA and lipids (Felgner et al., PNAS 84 (1987) 7413), the use of liposomes (Fraley et al., J. Biol. Chem. 255 (1980) 10431), and the like. More recently, the use of viruses as vectors for gene transfer has been seen to be a promising alternative to these physical transfection techniques. In this connection, different viruses have been tested for their capacity to infect certain cell populations. This applies especially to retroviruses (RSV, HMS, MMS, and the like), the HSV virus, adeno-associated viruses and adenoviruses.

The present invention constitutes a novel therapeutic approach to the treatment of pathologies associated with dyslipoproteinaemias, consisting in transferring and expressing in vivo genes coding for lipases involved in lipoprotein metabolism. It is especially advantageous that applicants have now shown that it is possible to construct recombinant viruses containing a DNA sequence coding for a lipase involved in lipoprotein metabolism, and to administer these recombinant viruses in vivo, and that this administration permits a stable and effective expression of a biologically active lipase in vivo, and without a cytopathological effect.

The present invention is also the outcome of the demonstration that adenoviruses constitute especially effective vectors for the transfer and expression of such genes. In particular, the present invention shows that the use of recombinant adenoviruses as vectors enables levels of expression of these genes to be obtained which are sufficiently high to produce the desired therapeutic effect.

The present invention thus affords a novel approach to the treatment and prevention of cardiovascular and neurological pathologies associated with dyslipoproteinaemias.

A subject of the invention lies in a defective recombinant virus comprising a nucleic acid sequence coding for a lipase involved in lipoprotein metabolism.

The subject of the invention is also the use of such a defective recombinant virus for the preparation of a pharmaceutical composition intended for the treatment and/or prevention of cardiovascular diseases.

The present invention also relates to the use of cells modified genetically in vivo or ex vivo with a virus as described above, or of cells producing such viruses, implanted in the body, permitting a sustained and effective in vivo release of a biologically active lipase.

DETAILED DESCRIPTION OF THE INVENTION

Figure 1:
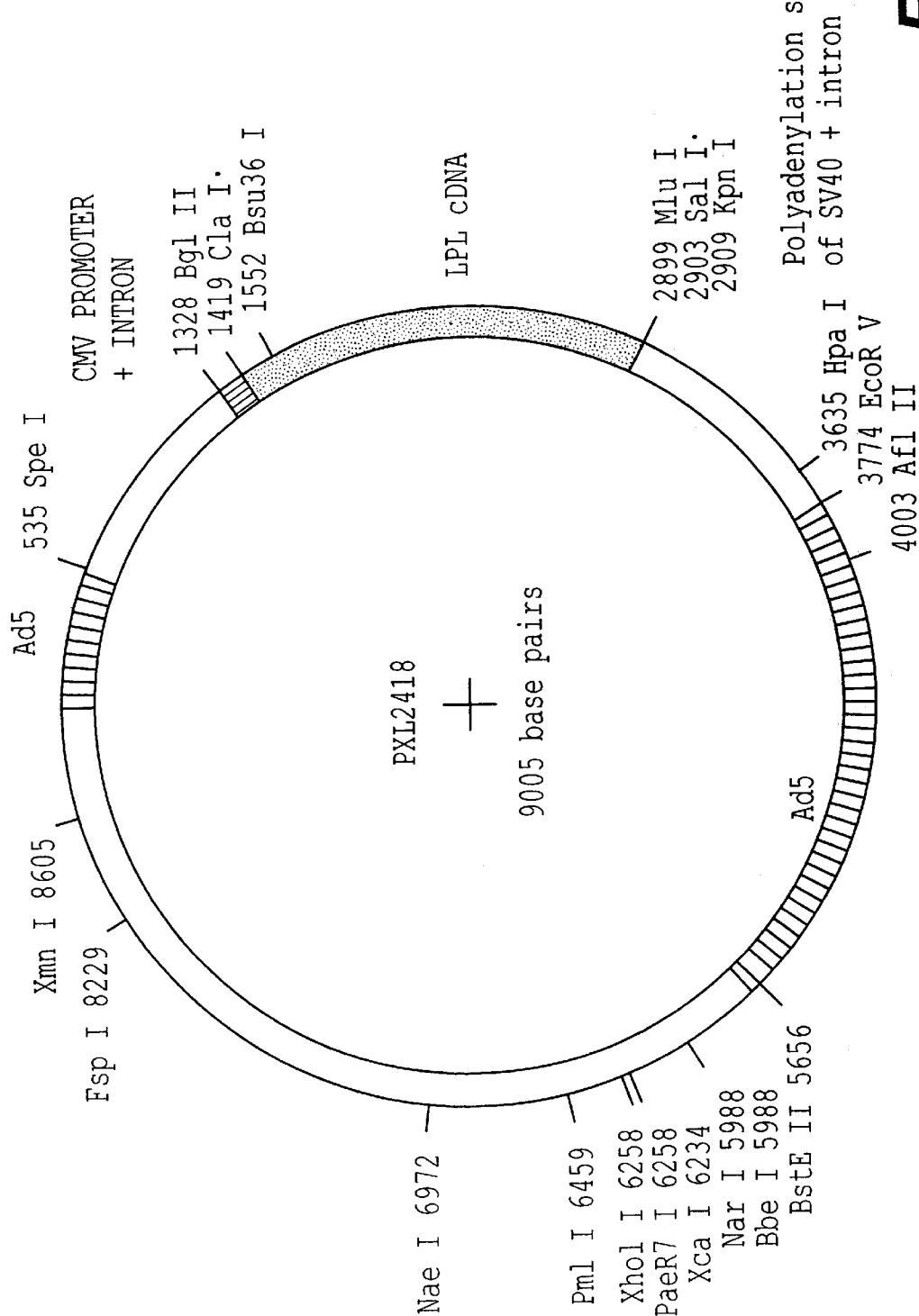
FIG. 1: Shows the structure of the vector pXL2418

Among lipases involved in lipoprotein metabolism for the purposes of the invention, preferential mention may be made of lipoprotein lipase (LPL).

Lipoprotein lipase (LPL) is an enzyme which permits the hydrolysis of triglycerides contained in very low density lipoproteins (VLDL) or chylomicrons.

Apolipoprotein CII, which is present at the surface of these particles, is used as cofactor in this hydrolysis. Naturally, LPL is mainly synthesized by adipocytes in the form of a 51-kDa monomeric precursor, which is then glycosylated (58 kDa). In the blood, LPL is active in dimeric form. Up to 80% of freshly synthesized LPL is degraded in the lysosomal compartment before being able to be secreted. After its secretion, LPL is taken up by the luminal face of the cells of the vascular endothelium, to which it binds via glycosaminoglycans. It has a very strong affinity for heparin, which enables LPL to be displaced from its binding site at the surface of the endothelial cell. Intravenous injection of heparin enables LPL concentration and activity to be measured in patients. LPL is utilized in the vascular cells and also in liver cells as an uptake agent for lipoproteins, increasing their retention at the cell surface and thereby promoting their uptake or their modification.

cDNA coding for human LPL has been cloned and sequenced (Wion et al., Science 235 (1987) 1638–1641). Two forms of messengers coexist, of 3350 and 3750 bases, mainly in adipose and muscle tissue, and originate from the use of 2 polyadenylation sites. They include a long untranslated 3' sequence and code for a preprotein of 475 aa, from which a leader sequence of 27 aa is cleaved to give rise to the mature monomeric protein of 448 residues. The LPL gene has also been cloned (Kirchgessner et al., Proc. Natl. Acad. Sci. USA, 1987, 262:9647–9651). The synthesis, processing and secretion of LPL are regulated in a complex manner during development and in response to hormonal stimuli. A sizeable part of this regulation is accomplished at transcriptional level (review in Auwerx et al., Critical Reviews in Clinical Laboratory Sciences, 1992, 29:243–268).

The present invention shows that it is possible to incorporate a DNA sequence coding for LPL in a viral vector, and that these vectors enable a biologically active (dimeric) mature form of LPL to be expressed and secreted effectively. More especially, the invention shows that in vivo expression of active LPL may be obtained by direct administration of an adenovirus or by implantation of a cell which is productive or genetically modified by an adenovirus or by a retrovirus incorporating such a DNA.

The vectors of the invention may be used, in particular, to correct LPL deficiencies due to mutations in the LPL gene. Such deficiencies are relatively common and can reach an incidence of 1:5,000–1:10,000 in some populations (S. Santamarina-Fojo, 1992, Cur. Op. lipid., 3:186–195). These deficiencies can result from a sizeable mutation in the gene, leading to the absence of LPL synthesis or to the synthesis of a truncated or highly modified protein. The existence has, in effect, been shown in some patients of mutations of the insertion, deletion or nonsense mutation type (review in S. Santamarina-Fojo, 1992, Cur. Op. lipid., 3:186–195). They can also result from a defect at the catabolic site, which may be due to mutations of the missense type in the gene. They can also result from modification both at the heparin-binding site and at the catalytic site. At the heterozygous stage, these deficiencies can represent a considerable proportion of the commonest hyperlipidaemias, including familial hypertriglycerinaemias, combined familial hyperlipidaemias and postprandial hyperlipidaemias.

The present invention is especially advantageous, since it enables an expression of LPL which is controlled and without a harmful effect to be induced in organs which are not normally affected by the expression of this protein. In particular, an altogether advantageous release is obtained by implantation of cells which produce vectors of the invention, or are infected in vivo or ex vivo with vectors of the invention.

The lipase activity produced in the context of the present invention can be a human or animal lipase. The nucleic acid sequence used in the context of the present invention can be a cDNA, a genomic DNA (gDNA), an ARN (in the case of retroviruses) or a hybrid construction consisting, for example, of a cDNA into which one or more introns might be inserted. Other possible sequences are synthetic or semi-synthetic sequences. It is especially advantageous to use a cDNA or a gDNA. In particular, the use of a gDNA permits better expression in human cells. To permit their incorporation in a viral vector according to the invention, these sequences are advantageously modified, for example by site-directed mutagenesis, especially for the insertion of suitable restriction sites. The sequences described in the prior art are not, in effect, constructed for a use according to the invention, and prior adaptations may prove necessary in order to obtain substantial expressions. In the context of the present invention, it is preferable to use a nucleic acid sequence coding for a human lipase. Moreover, it is also possible to use a construction coding for a derivative of these lipases, especially a derivative of human LPL and HL. HL (hepatic lipase) is localized at the surface of hepatic endothelial cells. It differs from LPL in its insensitivity to the activating action of apoC-II. HL is involved in the hydrolysis of IDL lipids, and also of HDL2 lipids, bringing about their conversion to HDL3.

A derivative of these lipases comprises, for example, any sequence obtained by mutation, deletion and/or addition relative to the native sequence, and coding for a product retaining lipase activity. These modifications may be carried out by techniques known to a person skilled in the art (see general techniques of molecular biology below). The biological activity of the derivatives thereby obtained may then be readily determined, as described, in particular, in Example 3. The derivatives for the purposes of the invention may also be obtained by hybridization from nucleic acid libraries, using the native sequence or a fragment of the latter as probe.

These derivatives are, in particular, molecules having a greater affinity for their binding sites, molecules displaying greater resistance to proteases, molecules having greater therapeutic efficacy or reduced side effects, or possibly novel biological properties. The derivatives also include modified DNA sequences permitting improved expression in vivo.

Among preferred derivatives, there may be mentioned, more especially, natural variants, molecules in which some N- or O-glycosylation sites have been modified or eliminated, molecules in which one or more residues have been substituted or molecules in which all the cysteine residues have been substituted (muteins). There may also be mentioned derivatives obtained by deletion of regions having little or no involvement in the interaction with the binding sites of interest or expressing an undesirable activity, and derivatives containing additional residues relative to the native sequence, such as, for example, a secretion signal and/or a junction peptide.

In a first embodiment, the present invention relates to a defective recombinant virus comprising a cDNA sequence coding for a lipase involved in lipoprotein metabolism. In another preferred embodiment of the invention, the DNA sequence is a gDNA sequence.

The vectors of the invention may be prepared from different types of virus. Preferably, vectors derived from adenoviruses, from adeno-associated viruses (AAV), from herpesviruses (HSV) or from retroviruses are used. It is most especially advantageous to use an adenovirus, for a direct administration or for the ex vivo modification of cells intended to be implanted or a retrovirus, for the implantation of productive cells.

The viruses according to the invention are defective, that is to say they are incapable of replicating autonomously in the target cell. Generally, the genome of the defective viruses used in the context of the present invention hence lacks at least the sequences needed for replication of the said virus in the infected cell. These regions may be either removed (wholly or partially), or rendered non-functional, or substituted by other sequences, and in particular by the nucleic acid sequence coding for the lipase. Preferably, the defective virus nevertheless retains the sequences of its genome which are needed for encapsidation of the viral particles.

As regards adenoviruses more especially, different serotypes, the structure and properties of which vary somewhat, have been characterized. Among these serotypes, it is preferable to use, in the context of the present invention, human adenoviruses type 2 or 5 (Ad 2 or Ad 5) or adenoviruses of animal origin (see Application WO 94/26914). Among adenoviruses of animal origin which are useable in the context of the present invention, adenoviruses of canine, bovine, murine (e.g.: Mavl, Beard et al., Virology 75 (1990) 81), ovine, porcine, avian or alternatively simian (e.g.: SAV) may be mentioned. Preferably, the adenovirus of animal origin is a canine adenovirus, and more preferably a CAV2 adenovirus [Manhattan or A26/61 (ATCC VR-800) strain, for example]. It is preferable to use adenoviruses of human or canine or mixed origin in the context of the invention.

Preferably, the defective adenoviruses of the invention comprise the ITRs, a sequence permitting encapsidation and the sequence coding for the lipase. Advantageously, in the genome of the adenoviruses of the invention, the E1 region at least is rendered non-functional. Still more preferably, in the genome of the adenoviruses of the invention, the E1 gene and at least one of the genes E2, E4, L1 -L5 are non-functional. The viral gene of interest may be rendered non-functional by any technique known to a person skilled in the art, and in particular by total elimination, substitution, partial deletion or addition of one or more bases in the gene or genes of interest. Such modifications may be obtained in vitro (on the isolated DNA) or in situ, for example by means of genetic engineering techniques, or alternatively by treatment by means of mutagenic agents. Other regions may also be modified, and in particular the E3 (WO 95/02697), E2 (WO 94/28938), E4 (WO 94/28152, WO 94/12649, WO 95/02697) and L5 (WO 95/02697) regions. According to a preferred embodiment, the adenovirus according to the invention comprises a deletion in the E1 and E4 regions, and the sequence coding for LPL is inserted in the inactivated E1 region. According to another preferred embodiment, it comprises a deletion in the E1 region, into which are inserted the E4 region and the sequence coding for LPL (see FR 94/13355).

The defective recombinant adenoviruses according to the invention may be prepared by any technique known to a person skilled in the art (Levrero et al., Gene 101 (1991) 195, EP 185,573; Graham, EMBO J. 3 (1984) 2917). In particular, they may be prepared by homologous recombination between an adenovirus and a plasmid carrying, inter alia, the DNA sequence coding for the lipase. Homologous recombination takes place after cotransfection of the said adenovirus and said plasmid into a suitable cell line. The cell line used should preferably (i) be transformable by the said elements, and (ii) contain the sequences capable of complementing the portion of the genome of the defective adenovirus, preferably in integrated form in order to avoid risks of recombination. As an example of a line, there may be mentioned the human embryonic kidney line 293 (Graham et al., J. Gen. Virol. 36 (1977) 59) which contains, in particular, integrated in its genome, the left-hand portion of the genome of an Ad5 adenovirus (12 %), or lines capable of complementing the E1 and E4 functions as are described, in particular, in Applications Nos. WO 94/26914 and WO 95/02697.

Thereafter, the adenoviruses which have multiplied are recovered and purified according to standard techniques of molecular biology, as illustrated in the examples.

Thereafter, the adenoviruses which have multiplied are recovered and purified according to standard techniques of molecular biology, as illustrated in the examples.

Adeno-associated viruses (AAV) are, for their part, relatively small-sized DNA viruses which integrate stably and in a site-specific manner in the genome of the cells they infect. They are capable of infecting a broad range of cells without inducing an effect on growth, morphology or cell differentiation. Moreover, they do not appear to be implicated in pathologies in man. The AAV genome has been cloned, sequenced and characterized. It comprises approximately 4,700 bases, and contains at each end an inverted repeat region (ITR) of approximately 145 bases, serving as origin of replication for the virus. The remainder of the genome is divided into 2 essential regions carrying the encapsidation ftmctions: The left-hand portion of the genome, which contains the rep gene involved in the viral replication and expression of the viral genes; the right-hand portion of the genome, which contains the cap gene coding for the capsid proteins of the virus.

The use of vectors derived from AAV for the transfer of genes in vitro and in vivo has been described in the literature (see, in particular, WO 91/18088; WO 93/09239; U.S. Pat. No. 4,797,368, U.S. Pat. No. 5,139,941, EP 488,528). These applications describe different constructions derived from AAV, in which the rep and/or cap genes are deleted and replaced by a gene of interest, and their use for transferring the said gene of interest in vitro (into cells in culture) or in vivo (directly into a body). However, none of these documents describes or suggests the use of a recombinant AAV for the transfer and expression of a lipase ex vivo or in vivo, or the advantages of such a transfer. The defective recombinant AAVs according to the invention may be prepared by cotransfection, into a cell line infected with a human helper virus (for encapsidation genes (rep and cap genes) of AAV. The recombinant AAVs produced are then purified by standard techniques.

Regarding herpes viruses and retroviruses, the construction of recombinant vectors has been amply described in the literature: see, in particular, Breakfield et al., New Biologist 3 (1991) 203; EP 453242, EP 178220, Bernstein et al., Genet. Eng.; 7 (1985) 235; McCormick, BioTechnology 3 (1985) 689, and the like.

In particular, retroviruses are integrative viruses which infect dividing cells. The retrovirus genome essentially comprises two LTRs, an encapsidation sequence and three coding regions (gag, pol and env). In the recombinant vectors derived from retroviruses, the gag, pol and env genes are generally deleted wholly or partially, and replaced by a heterologous nucleic acid sequence of interest. These vectors may be produced from different types of retrovirus such as, in particular, MoMuLV (Moloney murine leukaemia virus; also designated MoMLV), MSV (Moloney murine sarcoma virus), HaSV (Harvey sarcoma virus), SNV (spleen necrosis virus), RSV (Rous sarcoma virus) or alternatively Friend virus.

To construct recombinant retroviruses containing a sequence coding for LPL according to the invention, a plasmid containing, in particular, the LTRs, the encapsidation sequence and the coding sequence is generally constructed, and then used to transfect a so-called encapsidation cell line capable of providing in trans the retroviral functions that are deficient in the plasmid. Generally, the encapsidation lines are capable of expressing the gag, pol and env genes. Such encapsidation lines have been described in the prior art, and in particular the line PA317 (US 4,861,719), the line PsiCRIP (WO 90/02806) and the line GP+envAm-12 (WO 89/07150).

Moreover, the recombinant retroviruses can contain modifications in the LTRs to eliminate transcriptional activity, as well as extended encapsidation sequences containing a portion of the gag gene (Bender et al., J. Virol. 61 (1987) 1639). The recombinant retroviruses produced are then purified by standard techniques.

To implement the present invention, it is most especially advantageous to use a defective recombinant adenovirus. The results given below demonstrate the especially advantageous properties of adenoviruses for expressing in vivo a protein having lipase activity. The adenoviral vectors according to the invention are especially advantageous for a direct administration of a purified suspension in vivo, or for the in vivo transformation of cells, in particular autologous cells, for the purpose of their implantation. Furthermore, the adenoviral vectors according to the invention possess, in addition, considerable advantages such as, in particular, their very high efficiency of infection, enabling infection to be carried out using small volumes of viral suspension.

In an especially preferred embodiment, an adenovirus containing, in addition to the gene coding for the lipase, a gene coding for an apolipoprotein is used according to the invention. The lipase is preferably hepatic lipase and the apolipoprotein is preferably selected from apoA-I and apoAIV. The two genes are advantageously used in the form of a bicistronic construction which is introduced into an adenoviral vector according to the protocol described above for the construction of an adenovirus containing a single gene. Advantageously, the invention relates to a recombinant adenovirus containing a gene coding for HL and a gene coding for ApoA-I, inserted into the E1 region. The adenovirus construction containing a gene coding for an apo has been described in Application PCT/FR94/00422, which is incorporated herein by reference.

According to another especially advantageous embodiment of the invention, a line is used which produces retroviral vectors containing the sequence coding for the lipase, for implantation in vivo. The lines which are usable for this purpose are, in particular, PA317 (U.S. Pat. No. 4,861,719), PsiCrip (WO 90/02806) and GP+envAm-12 (U.S. Pat. No. 5,278,056) cells, modified to permit the production of a retrovirus containing a nucleic acid sequence coding for a lipase according to the invention.

Advantageously, in the vectors of the invention, the sequence coding for the lipase is placed under the control of signals permitting its expression in infected cells. These signals can be ones for homologous or heterologous expression, that is to say signals different from the ones naturally responsible for the expression of the lipase. They can, in particular, be sequences responsible for the expression of other proteins, or synthetic sequences. In particular, they can be sequences of eukaryotic or viral genes or derived sequences, stimulating or repressing the transcription of a gene, specifically or non-specifically and inducibly or non-inducibly. As an example, they can be promoter sequences originating from the genome of the cell which it is desired to infect, or from the genome of a virus, and in particular the promoters of the adenovirus E1A and MLP genes, the CMV, RSV LTR promoter, and the like. Among eukaryotic promoters, there may also be mentioned the ubiquitous promoters (HPRT, vimentin, α-actin, tubulin, and the like), the promoters of intermediate filaments (desmin, neurofilaments, keratin, GFAP, and the like), the promoters of therapeutic genes (MDR, CFTR, factor VIII type, and the like), tissue-specific promoters (pyruvate kinase, villin, promoter of the fatty acid-binding intestinal protein, α-actin promoter of smooth muscle cells, promoters specific to the liver; Apo AI, Apo AII, human albumin, and the like) or alternatively promoters responding to a stimulus (steroid hormone receptor, retinoic acid receptor, and the like). In addition, these expression sequences may be modified by adding activation, regulatory, and the like, sequences. Moreover, when the inserted gene does not contain expression sequences, it may be inserted into the genome of the defective virus downstream of such a sequence.

In a particular embodiment, the invention relates to a defective recombinant virus comprising a nucleic acid sequence coding for a lipase involved in lipoprotein metabolism, under the control of a promoter chosen from RSV LTR or the CMV early promoter.

More preferably, the nucleic acid sequence used also comprises signals permitting secretion of the lipase by infected cells. To this end, the nucleic acid sequence generally contains, upstream of the coding sequence, a signal sequence directing the lipase synthesized into the pathways of secretion of the infected cell. This signal sequence can be the natural signal sequence of the lipase synthesized, but it can also be any other signal sequence which is functional in the infected cell, or an artificial signal sequence.

As stated above, the present invention also relates to any use of a virus as described above for the preparation of a pharmaceutical composition intended for the treatment and/or prevention of pathologies associated with dyslipoproteinaemias.

The present invention also relates to a pharmaceutical composition comprising one or more defective recombinant viruses as are described above. These pharmaceutical compositions may be formulated with a view to topical, oral, parenteral, intranasal, intravenous, intramuscular, subcutaneous, intraocular, transdermal, and the like, administration. Preferably, the pharmaceutical compositions of the invention contain a pharmaceutically acceptable vehicle for an injectable formulation, in particular for an intravenous injection, such as, for example, into the patient's portal vein. The formulations can be, in particular, isotonic steryl solutions, or dry, in particular lyophilized, compositions which, on adding sterilized water or physiological saline, as the case may be, enable injectable solutions to be produced. Direct injection into the patient's portal vein is advantageous, since it enables the infection to be targeted to the liver, and thus the therapeutic effect to be concentrated in this organ.

The doses of defective recombinant virus used for the injection may be adapted in accordance with different parameters, and in particular in accordance with the viral vector, the mode of administration used, the pathology in question or alternatively the desired period of treatment. Generally speaking, the recombinant adenoviruses according to the invention are formulated and administered in the form of doses of between $10^4$ and $10^{14}$ pfu/ml, and preferably $10^6$ to $10^{10}$ pfu/ml. The term pfu (plaque forming unit) corresponds to the infectious power of a solution of virus, and is determined by infecting a suitable cell culture and measuring, generally after 48 hours, the number of plaques of infected cells. The techniques of determination of the pfu titre of a viral solution are well documented in the literature.

As regards retroviruses, the compositions according to the invention can contain the productive cells directly, with a view to their implantation.

In this connection, another subject of the invention relates to any mammalian cells infected with one or more defective recombinant viruses as are described above. More especially, the invention relates to any human cell population infected with these viruses. The cells in question can be, in particular, fibroblasts, myoblasts, hepatocytes, keratinocytes, endothelial cells, glial cells, and the like.

The cells according to the invention can originate from primary cultures. They may be removed by any technique known to a person skilled in the art and then set up in culture under conditions permitting their proliferation. As regards fibroblasts, more especially, the latter may be readily obtained from biopsies, for example according to the technique described by Ham [Methods Cell. Biol. 21a (1980) 255]. These cells may be used directly for infection with the viruses, or stored, for example by freezing, to establish autologous banks with a view to subsequent use. The cells according to the invention can also be secondary cultures obtained, for example, from pre-established banks (see, for example, EP 228458, EP 289034, EP 400047, EP 456640).

The cells in culture are then infected with the recombinant viruses to endow them with the capacity to produce a biologically active lipase. Infection is carried out in vitro according to techniques known to a person skilled in the art. In particular, depending on the cell type used and the desired number of copies of virus per cell, a person skilled in the art can adapt the multiplicity of infection and, where appropriate, the number of infection cycles carried out. It should be obvious that these steps must be performed under suitable conditions of sterility when the cells are intended for administration in vivo. The doses of recombinant virus used for infecting the cells may be adapted by a person skilled in the art in accordance with the desired objective. The conditions described above for in vivo administration may be applied to infection in vitro. For infection with retroviruses, it is also possible to coculture the cells which it is desired to infect with cells producing the recombinant retroviruses according to the invention. This makes it possible to eliminate the need to purify the retroviruses.

Another subject of the invention relates to an implant comprising mammalian cells infected with one or more defective recombinant viruses as are described above, or cells which produce recombinant viruses, and an extracellular matrix. Preferably, the implants according to the invention comprise $10^5$ to $10^{10}$ cells. More preferably, they comprise $10^6$ to $10^8$ cells.

More especially, in the implants of the invention, the extracellular matrix comprises a gelling compound and, where appropriate, a support permitting anchorage of the cells.

For the preparation of the implants according to the invention, different types of gelling agents may be employed. The gelling agents are used for inclusion of the cells in a matrix having the constitution of a gel, and to promote anchorage of the cells to the support, where appropriate. Different cellular adhesion agents may hence be used as gelling agents, such as, in particular, collagen, gelatin, glycosaminoglycans, fibronectin, lectins, and the like. Preferably, collagen is used in the context of the present invention. The collagen may be of human, bovine or murine origin. More preferably, type I collagen is used.

As stated above, the compositions according to the invention advantageously comprise a support permitting anchorage of the cells. The term anchorage denotes any form of biological and/or chemical and/or physical interaction bringing about adhesion and/or binding of the cells to the support.

Moreover, the cells can either coat the support used or enter the interior of this support, or both. It is preferable, in the context of the invention, to use a non-toxic and/or biocompatible solid support. In particular, polytetrafluoroethylene (PTFE) fibres or a support of biological origin may be used.

The implants according to the invention may be implanted in different sites of the body. In particular, the implantation may be performed in the peritoneal cavity, in the subcutaneous tissue (subpubic region, iliac or inguinal fossae, and the like), in an organ, a muscle, a tumour or the central nervous system, or alternatively under a mucosa. The implants according to the invention are especially advantageous in that they enable the release of the lipase in the body to be controlled: this is, in the first place, determined by the multiplicity of infection and by the number of cells implanted. The release can then be controlled either by withdrawing the implant, which stops the treatment permanently, or by the use of regulable expression systems enabling the expression of the therapeutic genes to be induced or repressed.

The present invention thus affords a very effective means for the treatment or prevention of pathologies associated with dyslipoproteinaemias, especially obesity, hypertriglyceridaemia or, in the field of cardiovascular complaints, myocardial infarction, angina, sudden death, cardiac decompensation and stroke.

In addition, this treatment can be applied equally well to man and to any animal such as sheep, cattle, domestic animals (dogs, cats, and the like), horses, fish, and the like.

The present invention also involves detecting a mutation in the gene coding for the enzyme lipoprotein lipase in a sample of DNA obtained from a patient.

The first step in the method in accordance with the invention is obtaining an appropriate sample of DNA. A suitable source of such a sample is from patient blood. Isolation of the DNA from the blood can be performed by many different methods. For example, the DNA may be isolated from the leukocytes using a salt-chloroform extraction as described in *Trends in Genetics* 5: 391 (1989).

Once the sample of patient DNA is obtained, it may be desirable to amplify a portion of the DNA including the region of interest. One technique which can be used for amplification is Polymerase Chain Reaction (PCR) amplification. This technique, which is described in U.S. Pat. Nos. 4,683,202 and 4,683,195, which are incorporated herein by reference, makes use of two amplification primers each of which hybridizes to a different one of the two strands of the DNA duplex at regions which do not overlap the site of the mutation being tested for, in this case the mutation in amino acid 291. Multiple cycles of primer extension, and denaturation are used to produce additional copies of DNA to which the primers can hybridize. This amplification can be performed in a solution, or on a solid support (see, e.g. U.S. Pat. No. 5,200,314 which is incorporated herein by reference).

The mutation site of interest is at a defined location within exon 6 of the lipoprotein lipase gene, the sequence of which is known in the art. Oka et al., *Biochim. Biophys. Acta* 1049: 21–26 (1990); Deeb et al., *Biochemistry* 28: 4131–4135 (1989); Wion et al., *Science* 235: 1638–1641 (1987). Amplification primers may be used which bind to the intron regions on either side of exon 6, or which bind to portions of exon 6 itself. Where amplification of the mutation site is desired, the primers should not overlap the site of the mutation of interest. Suitable primers include those described for exon 6 in Monsalve et al., *J Clin. Invest.* 86: 728–734 (1990).

Figure 6:
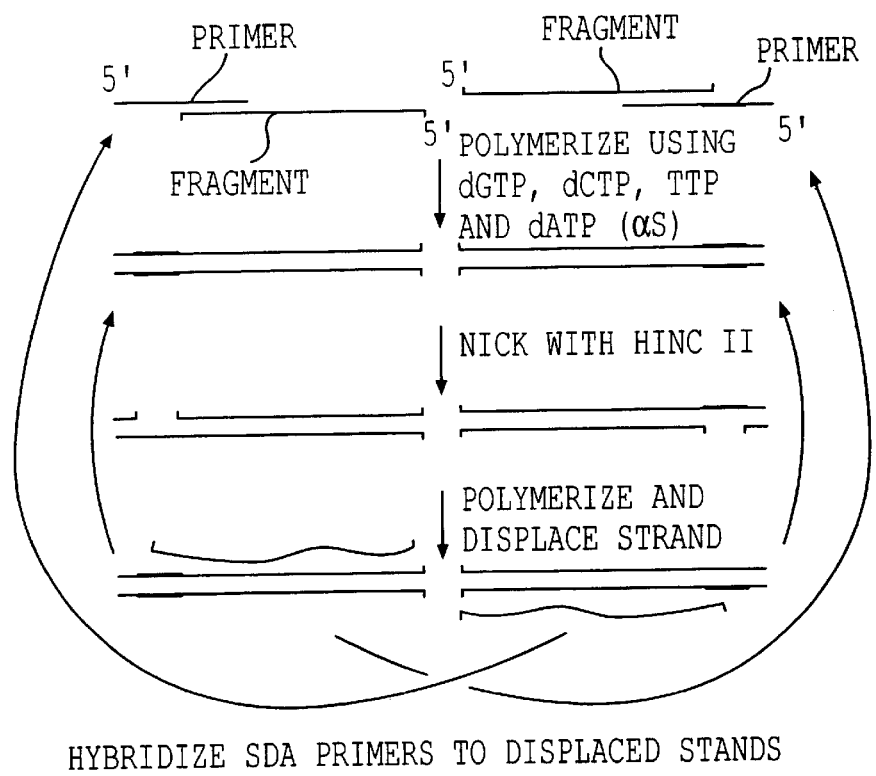
FIG. 6 illustrates the use of strand displacement amplification in a method in accordance with the present invention.

Another amplification technique which may be used in accordance with the present invention is known as Strand Displacement Amplification (SDA). In this technique, which is described in U.S. Pat. No. 5,270,184, incorporated herein by reference, and EP 0 497 272, and which is exemplified in FIG. 6, a gene fragment is used as the target, and a primer is used which binds to the 3'-end of this fragment. The primer is selected to include a restriction site near its 5'-end. This can be achieved by using a primer which extends beyond the 3'-end of the target gene fragment if there is no restriction site conveniently located towards the 3'-end of the fragment from the site of interest. The primer and the target fragment (if the primer extends beyond the end of the fragment) are extended to form a duplex using modified nucleoside feedstocks, e.g., α-thio nucleoside triphosphates, at least in the region of the restriction cleavage site so that the newly formed strand is not susceptible to cleavage by the endonuclease. For subsequent amplification normal feedstocks are used. A restriction endonuclease is introduced which nicks the duplex at the restriction site. Extension then starts over at the site of the nick, at the same time that the previously hybridized oligonucleotide is displaced. In this way, multiple copies of one or both strands of a gene or gene fragment can be amplified without the use of temperature cycling. To use strand displacement amplification to amplify the mutation site responsible for the Asn291 Ser mutation, primers flanking exon 6, such as those described in Monsalve et al. could be used.

Once amplified, the DNA may be evaluated by any of a number of methods to determine if the Asn291 Ser mutation is present. First, the amplified DNA can be sequenced (optionally after cloning into a TA cloning vector, available from Invitrogen, Inc.) using manual or automated sequencing of the amplified product. Since the complete sequence of exon 6 of normal lipoprotein lipase is known, targeted sequencing primers can be readily developed for this purpose.

Another approach to the detection of Asn291 Ser mutations, generally used following amplification, is the use of sequence specific oligonucleotide probes which bind to one of the mutant or wildtype form, but not to the other. Such probes generally have a length of 15 to 20 bases. Because the difference being evaluated is a single base, the analysis is conducted under very stringent hybridization conditions such that only perfect matches will form stable hybrids.

The probe used in the invention is advantageously labeled to permit its easy detection. Suitable labels include radioactive labels, fluorescent labels, and reactive labels such as biotin. The probe may also be labeled twice, for example with a radiolabel and a reactive label, in which case the reactive label may be used to the capture the DNA hybrid, for example through the reaction of biotin with an avidin-coated support.

A preferred format for testing using sequence specific probes involves the use of a sandwich assay in which the amplified DNA is evaluated using two probes. The first oligonucleotide probe is either selected to bind specifically to a gene encoding a mutant human lipoprotein lipase having a serine residue as amino acid 291, wherein said probe binds to a portion of the gene including the bases coding for the serine residue or selected to bind specifically to a gene encoding a normal human lipoprotein lipase having an asparagine residue as amino acid 291, wherein said probe binds to a portion of the gene including the bases coding for the asparagine residue. The second oligonucleotide probe is selected to bind to a different, non-overlapping portion of the human-LPL gene which is the same in both mutant and non-mutant forms. One of the two probes is labeled with a detectable label while the other is labeled with a reactive label to facilitate immobilization. Only when both probes are bound to a single piece of amplified DNA will the detectable label be immobilized through the formation of a sandwich of the structure shown in FIG. 2.

Various modifications of the amplification process may also be used in accordance with the present invention to detect the presence of an Asn29 1 Ser mutation. If intentionally mismatched primers are used during the amplification, the amplified nucleic acids may also be evaluated for the presence of the Asn291 Ser mutation using a technique called restriction fragment length polymorphism (RFLP). In order to make use of RFLP directly to detect a point mutation (as opposed to an insertion or deletion mutation), the mutation must result in the addition or loss of a site cleaved by a restriction endonuclease. If this is the case, the fragments produced upon restriction endonuclease digestion of the normal and mutant gene differ in number, in size, or in both. This difference can be detected by gel electrophoresis of the restriction fragments.

In the case of the Asn291 Ser mutation, the nucleotide sequence of the coding strand changes from

5'- - - GAG ATC AAT AAA GTC - - - 3' SEQ. ID. NO: 6 to

5'- - - GAG ATC AGT AAA GTC - - - 3' SEQ. ID. NO: 7

Figure 8:
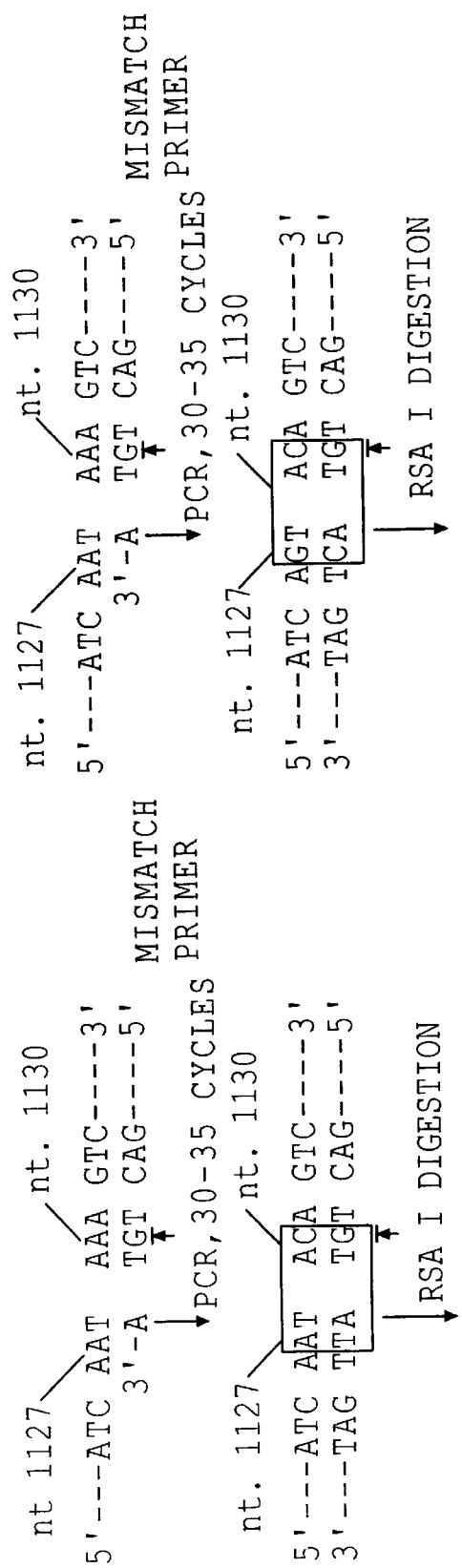
FIG. 8 illustrates the use of mismatch primers in accordance with the invention to detect the Asn291 Ser mutation.

These fragments lack the two-fold symmetry that is associated with cleavage sites of restriction endonucleases, and thus one cannot simply use an enzyme which will cleave one of the sequences, but not the other. RFLP can be used, however, if a special mismatch primer is used during the amplification process. This primer, shown below in Example 8, binds to the LPL gene at a site adjacent to the mutation of interest, and introduces an intentional error into the amplified DNA. Thus, as illustrated in FIG. 8, instead of the expected sequence, the mismatch primer produces the duplex region 5'- - - ATAC - - - 3' coding strand
3'- - - TATG - - - 5' non-coding strand
when a wild-type gene is amplified, and the sequence
5'- - - GTAC - - - 3' coding strand
3'- - - CATG - - - 5' non-coding strand
when a mutant gene is amplified, where the C/G pair in the fourth position of the above fragments is the intentional mismatch. Amplified mutant genes therefore contain a restriction site (5'-GTAC-3') which is cleaved by the restriction endonuclease RsaI, but amplified wild-type sequence (5'-ATAC-3') does not. Thus, a polymorphism measurable through restriction fragment lengths is artificially introduced into the amplified DNA using the mismatch primers.

The amplification process may also be modified by using labeled primers which facilitate detection and/or capture of the amplified product. For example, as described in British Patent No. 2 202 328, using a biotin-labeled primer as one of the two primers permits the recovery of the extended primers produced during the amplification reaction, e.g., by binding the extended primers to a support coated with (strept)avidin. If the primer used is in a region flanking the mutation site, the presence of the mutation can be detected by adding a labeled probe, which specifically binds to the mutant or wild-type gene, to the biotinylated amplified DNA either before or after capture of the amplified DNA on a support. If the label becomes bound to the support, this indicates that the probe was bound. Alternatively, the primer may be one which spans the mutation site in which case amplification will occur using a primer corresponding to the mutant sequence only when the mutation is present (and vice versa). In this case, a labeled probe which binds to a portion of the LPL gene away from the mutation site or labeled nucleoside feedstocks may be used to introduce a label into the amplified DNA.

The presence of the Asn291 Ser mutation may also be detected using a catalytic hybridization amplification system of the type described in International Patent Publication No. WO89/09284, which is incorporated herein by reference. Basically, in this technique, the target nucleic acid acts as a cofactor for enzymatic cleavage of probe oligonucleotides. Thus, a substantial excess of labeled probe oligonucleotide (which binds specifically to either the mutant or the wild-type gene) is combined with the target nucleic acid under stringent hybridization conditions such that only exactly complementary strands will hybridize to any measurable extent. An enzyme is added which will cleave the probe when it is part of a duplex, but not in single stranded form. The mixture is then cycled through multiple cycles of annealing/enzyme digestion and denaturation. If the probe binds to the target, the result is the production of many small labeled probe-fragments, and the concurrent reduction in the number of full-size labeled probes. Either the increase in the number of fragments or the decrease in the number of full-sized probes can be detected and provides an amplified indication of the presence or absence of the target sequence in the sample.

An example of an enzyme which can be used in the catalytic hybridization amplification system is RNaseH which is used in combination with RNA probes; which are selectively cleaved when hybridized to a strand of target DNA. Restriction endonucleases which do not cleave phosphorothioate-modified DNA may also be used, provided that the target DNA is first copied to produce a phosphorothioate-modified target. Because this method combines both amplification and detection, prior amplification of the genomic DNA from the sample is generally not necessary.

Another technique useful in the present invention which combines amplification and detection relies on the autocatalytic replication of certain RNA's as described in U.S. Pat. No. 4,957,858, which is incorporated herein by reference. Briefly, in this technique a replicative RNA segment is ligated to a sequence specific oligonucleotide probe which binds to either the mutant or the wild-type form of the Asn291 Ser mutation site in exon 6 of the LPL gene. This ligated probe is then combined with the genomic DNA in such a manner that the probe will bind if the matching sequence is present in the genomic DNA, and so that unbound probe can be separated from bound probe. For example, the genomic DNA may be immobilized on a solid support to facilitate washing out of unbound probe molecules. Thereafter, the RNA portion of the ligated probe is amplified, for example using the enzyme Q-beta replicase.

Yet another form of combination amplification/detection technique which is useful in the present invention is described in U.S. Pat. No. 5,124,246 which is incorporated herein by reference. In this technique, a total of five types of oligo-nucleotide probes are used. The first type of probe is a multimer oligonucleotide having a "star" type configuration with many generally identical arms. The second type of probe is a labeling probe. The labeling probe is complementary to the sequence of one of the arms of the multimer probe and includes a detectable label. The third type of probe is an immobilized probe. A plurality of this third type of probe is affixed to a solid support. The specific sequences used in these first three types of probes are independent of the nature of DNA being analyzed, except that they should not hybridize with this DNA directly.

The fourth type of probe is referred to as an amplifier probe. These probes are synthesized in two parts, one which is complementary to a portion of the normal sequence of exon 6 of the LPL gene away from the Asn291 Ser mutation site, and one which is complementary to an arm of the multimer probe. A plurality of different types of amplifier probes is formed. These various types of probes are complementary to different, non-overlapping portions of the sequence. The fifth type of probe is a capture probe. The capture probe is also formed in two parts: one which is complementary to the site of the Asn291 Ser mutation and one which is complementary to the immobilized probe.

The assay is performed by combining denatured genomic DNA with the plurality of amplifier probes and capture probes under conditions permitting hybridization. The result is the binding of numerous amplifier probes to exon 6 of the LPL gene. The capture probe will only bind, however, if the corresponding mutant (or non-mutant, depending on the sequence of the probe) is present. Thereafter, the solid support having the third probe immobilized thereon is introduced. A solid support-immobilized probe-capture probe-genomic DNA-amplifier probe sandwich will form if DNA complementary to the capture probe is present. The support is then washed to remove unbound material, and the multimer probe is added. The multimer probe binds to the support via the amplification probe only if the sandwich was formed in the first place. The support is then washed and a labeling probe is added. The labeling probe will bind to all of the available arms of the multimer probe on the solid support, thus providing numerous detectable labels for each actual mutation site in the DNA sample.

In the foregoing discussion of amplification and detection techniques, there is frequent mention of labeled probes or labeled primers. For purposes of this application, the label applied to the primer may take any form, including but not limited to radiolabels; fluorescent or fluorogenic labels; colored or chromogenic labels; chemically reactive labels such as biotin; enzyme-labels, for example phosphatase, galactosidase or glucosidase enzymes which can produce colored or fluorescent reaction product in combination with substrates such as p-nitrophenyl phosphate (colored reaction product) or 4-methyl umbelliferyl phosphate (fluorescent cleavage product); and chemiluminescent labels.

A further aspect of the present invention is the particular oligonucleotide probes which may be used in one or several of the techniques as discussed above for detection of the Asn291 Ser mutation. Thus, for use in the case of mismatch primer amplification followed by RFLP analysis there is provided an oligonucleotide primer which binds specifically to a gene encoding for human lipoprotein lipase in a region adjacent to, but not overlapping the second base in the codon corresponding to residue 291 in human lipoprotein lipase, and which includes a mismatched base which does not correspond to the normal sequence of human lipoprotein lipase, whereby upon extension of the primer, using a target human lipoprotein lipase gene as a template, an extension product is produced which contains a restriction site which can be cleaved by a restriction endonuclease when the lipoprotein lipase product made by the target gene has a serine residue as amino acid 291, and does not contain such a restriction site when the lipoprotein lipase product made by the target gene has an asparagine residue as amino acid 291. A preferred primer which binds to the coding strand is one in which a base complementary to base number 1130 is changed from the normal thymine to guanine. For the non-coding strand, the change is from adenine to cytosine. A particularly preferred mismatch primer for binding to the coding strand has the sequence

CTG CTT CTT T TG GCT CTG AC T GTA SEQ. ID NO: 8.

For several of the detection methods discussed above, an oligonucleotide probe is utilized which binds to a site which includes the site of the specific mutation of interest. Thus, the present invention encompasses two types of oligonucleotide probes: (1) an oligonucleotide probe selected to bind specifically to a gene encoding a mutant human lipoprotein lipase having a serine residue as amino acid 291, wherein said probe binds to a portion of the gene including the bases coding for the serine residue; and (2) an oligonucleotide probe selected to bind specifically to a gene encoding a normal human lipoprotein lipase having a asparagine residue as amino acid 291, wherein said probe binds to a portion of the gene including the bases coding for the asparagine residue. These probes are preferably from 15 to 20 bases in length, and may be selected to bind to either the coding or the non-coding strand of the genomic DNA. Further, the probes will advantageously include a detectable label.

A further aspect of the present invention is a kit which may be used to detect the presence of the Asn291Ser mutation. The specific components of the kit will depend on the nature of the evaluation being conducted. In general, however, the kit will include a pair of primers selected to amplify a region of a human lipoprotein lipase gene encoding for amino acid 291 of human lipoprotein lipase. These primers may be primers for PCR, primers adapted for strand displacement amplification, or a normal primer and a mismatch primer. In addition, the kit may include oligonucleotide probes for use in the detection of the Asn291 Ser mutation.

The discovery of the significance of the Asn291 Ser mutation opens the door to the possibility of providing gene therapy to individuals having this mutation and thus to prevent or delay the onset of coronary artery disease and particularly premature atherosclerosis. In addition, since gene therapy to correct this defect would provide a patient with a fully functional lipoprotein lipase enzyme, therapeutic agents and methods used for this purpose may also be used effectively for other conditions associated with LPL mutations. Such conditions include infantile failure to thrive, hepatosplenomegaly, eruptive xanthomas, chronic and/or episodic abdominal pain, pancreatitis and lactescent plasma due to an accumulation of chylomicrons and very low density lipoproteins or their remnants in the plasma.

Gene therapy to introduce functional LPL may reduce the clinical manifestations stemming from hypertriglyceridemia in both LPL deficient homozygotes and heterozygotes. This gene transfer can be accomplished, as previously described, using adenovirus-DNA-polylysine conjugates; adenovirus constructs in which the normal LPL gene is inserted into the viral genome; or retroviral constructs in which the normal LPL gene is inserted into the viral genome. The vector may be introduced directly, for example by parenteral injection into the patient, or may be introduced via an implanted pseudo-organ.

Figure 9:
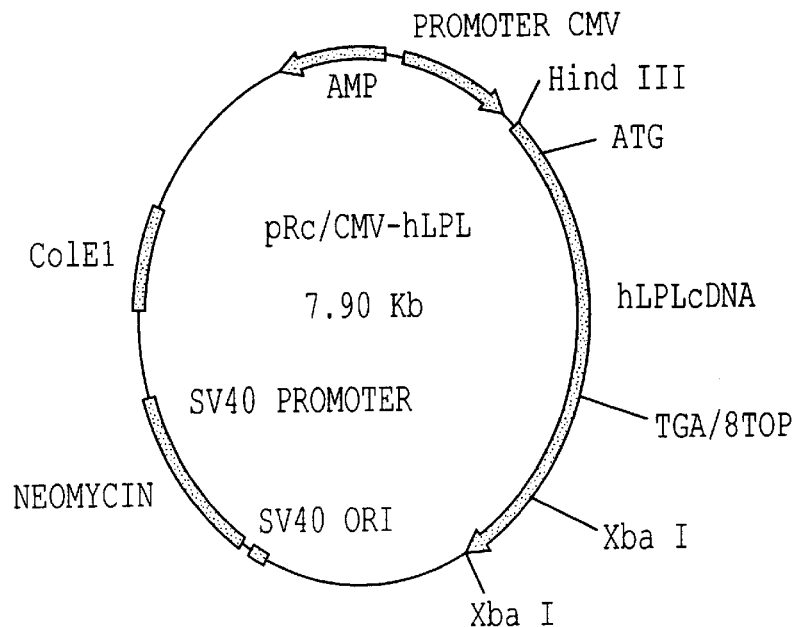
FIG. 9 shows a plasmid construct, PRc/CMV-hLPL useful in accordance with the present invention.
Figure 7:
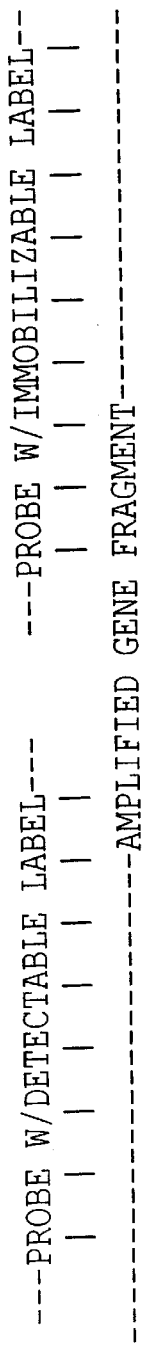
FIG. 7 shows the sandwich formed when two oligonucleotide probes are used to analyze for the presence of an Asn291 Ser mutation.

FIG. 9 shows a plasmid construct useful in accordance with the present invention. As shown, the plasmid pRc/CMV-hLPL is 7.90 Kbases in size. The preparation of this particular plasmid is described below in Example 9. It will be appreciated by persons skilled in the art, however, that variations in this technique, or the precise structure of the plasmid may be made without departing from the present invention provided that the plasmid contains a functional h-LPL gene and an appropriate promoter. For example, tissue-specific promoters, particularly adipose tissue specific or muscle specific promoters might be used in place of the CMV promoter. Furthermore, while the SV40 promoter and the antibiotic resistance markers are convenient for research purposes, they are not necessary for therapeutic purposes.

To prepare a plasmid for transfection into mammalian, and particularly human cells, the plasmid is complexed with an adenovirus-polylysine conjugate. In general this process involves the harvesting and purification of a suitable adenovirus, for example a virus which is incompetent as a result of an E1A or an E3 deletion mutation. The purified virus is then conjugated with a polycationic material for associating with DNA such as polylysine, polyarginine or protamine, for example using a bifunctional reagent such as ethyl-3,3-dimethyl aminopropyl carbodiimide (EDC) as a crosslinking agent. When the resulting adenovirus-polylysine conjugate is combined with a plasmid containing a normal LPL gene, an adenovirus-DNA-polylysine complex forms spontaneously. This complex transfects mammalian cells of various types when placed in media with the cells with relatively high efficiency, and the transfected cells produce functional LPL.

Mammalian cells may also be transduced (or transfected) using an adenovirus into which a gene encoding for normal LPL has been inserted. Preferred adenoviruses are those with an El or an E3 deletion mutation rendering the virus incompetent. The h-LPL gene can be conveniently inserted into the virus at the site of the deletion.

Specific modified adenoviruses useful in the present technique are based on the RSV β-Gal adenovector described by Stratford-Perricaudet et al., *J Clin. Invest.* 90 : 626–630 (1990). This adenovector is based on adenovirus Ad5. Human LPL cDNA is introduced into the vector by homologous recombination using a modified form of Strafford-Perricaudet's pLTRβGalpIX plasmid. The plasmid contains an RSV LTR promoter or a CMV plus intron promoter, human LPL cDNA, a poly A site plus small intron from SV40 derived from a pSV2 vector. Mulligan et al., *Science* 209: 1422–1427 (1980) which are inserted between nucleotides 455 to 3329 of an Ad5 DNA which is also deleted in the E3 region. This results in the deletion of E1A and part of E1B, but, leaves pIX intact. The resulting adenoviruses are non-replicating but can be propagated in 293 cells which transcomplement the E1A activity.

A third type of vector which may be used to transduce (or transfect) mammalian cells is a retroviral vector. Suitable vectors include myeloproliferative sarcoma virus (MPSV)-based retroviral vectors into which human LPL cDNA is inserted under the transcriptional control of the constitutive enhancer-promoter regulatory elements of the MPSV long terminal repeat (LTR).

Gene transfer vectors can be introduced into a human subject either in vivo or ex vivo. In the case of an in vivo treatment, the gene transfer vector may be simply injected into the patient, for example parenterally, and allowed to find suitable target cells. In the case of ex vivo treatment, cells are grown in vitro and transduced or transfected with the virus, embedded in a carrier such as a collagen matrix, which is then implanted in the patient, for example as a subcutaneous implant. Preferred cells for use in ex vivo applications are fibroblast cells taken from the patient who will receive the implant.

General Techniques of Molecular Biology

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, phenol or phenol/chloroform extraction of proteins, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

Plasmids of the pBR322 and pUC type and phages of the M13 series are of commercial origin (Bethesda Research Laboratories).

To carry out ligation, the DNA fragments may be separated according to their size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

The filling in of 5' protruding ends may be performed with the Klenow fragment of *E.coli* DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

Mutagenesis directed in vitro by synthetic oligodeoxynucleotides may be performed according to the method developed by Taylor et al. [Nucleic Acids Res. 13 (1985) 8749–8764] using the kit distributed by Amersham.

The enzymatic amplification of DNA fragments by the so-called PCR [Polymerase-catalysed Chain Reaction, Saiki R. K. et al., Science 230 (1985) 1350–1354; Mullis K. B. and Faloona F. A., Meth. Enzym. 155 (1987) 335–350] technique may be performed using a DNA thermal cycler (Perkin Elmer Cetus) according to the manufacturer's specifications.

The verification of the nucleotide sequences may be performed by the method developed by Sanger et al. [Proc. Natl. Acad. Sci. U.S.A, 74 (1977) 5463–5467] using the kit distributed by Amersham.

The present invention will be described more completely by means of the examples that follow, which one should consider as illustrative and non-limiting.

EXAMPLE 1

Construction of the Vector pXL2418 Carrying the Gene Coding for LPL Under the Control of the Cytomegalovirus (CMV) Early Promoter (FIG. 1)

This example describes the construction of a vector comprising a cDNA sequence coding for LPL, under the control of a promoter consisting of the cytomegalovirus (CMV) early promoter, as well as a region of the Ad5 adenovirus genome permitting homologous recombination. This vector was constructed as described below.

1.1. Construction of the Vector pXL2375

The vector pXL2375 contains, in particular, a region of the Ad5 adenovirus genome and a DNA sequence coding for apolipoprotein Al under the control of the CMV promoter. More especially, the CMV promoter used extends as far as the donor 5' splicing site linked to the 107 bp nearest the 3' end of the synthetic intron described by O'Gorman et al. (Science 251 (1991) 1351). The construction of this vector has been described in detail in copending Application FR 93/05125. It is understood that similar constructions may be carried out by a person skilled in the art.

1.2. Construction of the cDNA Sequence Coding for LPL

Plasmid pHLPL 26-1 described by Wion et al. (Science 235 (1987) 1638–1641) contains an incomplete sequence of LPL cDNA. Thus, this plasmid contains bases 272 to 1623 of LPL cDNA flanked by two EcoRI sites, cloned to the EcoRI site of a plasmid pGEMI (Promega).

The EcoRI fragment of pHLPL 26-1 containing the partial LPL cDNA was recloned into the EcoRI site of a plasmid pMTL22 (Chambers et al., Gene, 1988, 68:138–149), in the orientation placing the 5' bases of the cDNA on the same side as the BglII site of pMTL22. The resulting plasmid was called pXL2402.

The RNA of human adipose tissues was then extracted according to the technique of Chromczynski and Sacchin (Anal. Biochem. 162 (1987) 156–159). From this RNA preparation, an amplification was carried out by RT-PCR so as to isolate the missing portion of the LPL cDNA. To this end, the following primers were used: Sq4541: TTA GAT CTA TCG ATA GAT GGA GAG CAA AGC CCC TG (SEQ ID NO: 1)

This primer makes it possible to introduce a BglII site as well as a ClaI site upstream of the ATG. Sq3810: TAC ATT CCT GTT ACC GTC CAG CCA TGG ATC (SEQ ID NO: 2)

The 260-bp PCR fragment obtained after 25 amplification cycles was then cloned into plasmid pCR-II (Invitrogen) and sequenced for verification. It was then introduced via the BglII and NcoI sites into the vector pXL2402, which reconstitutes a complete cDNA preceded by a ClaI site and followed by a SalII site. The resulting plasmid was called pXL2417.

1.3. Construction of the Vector pXL2418.

Lastly, the LPL cDNA was inserted into plasmid pXL2375 between the SalI and ClaI sites, following excision of the Apo A1 cDNA with these same two enzymes. The plasmid obtained was designated pXL2418 (FIG. 1).

EXAMPLE 2

Figure 2:
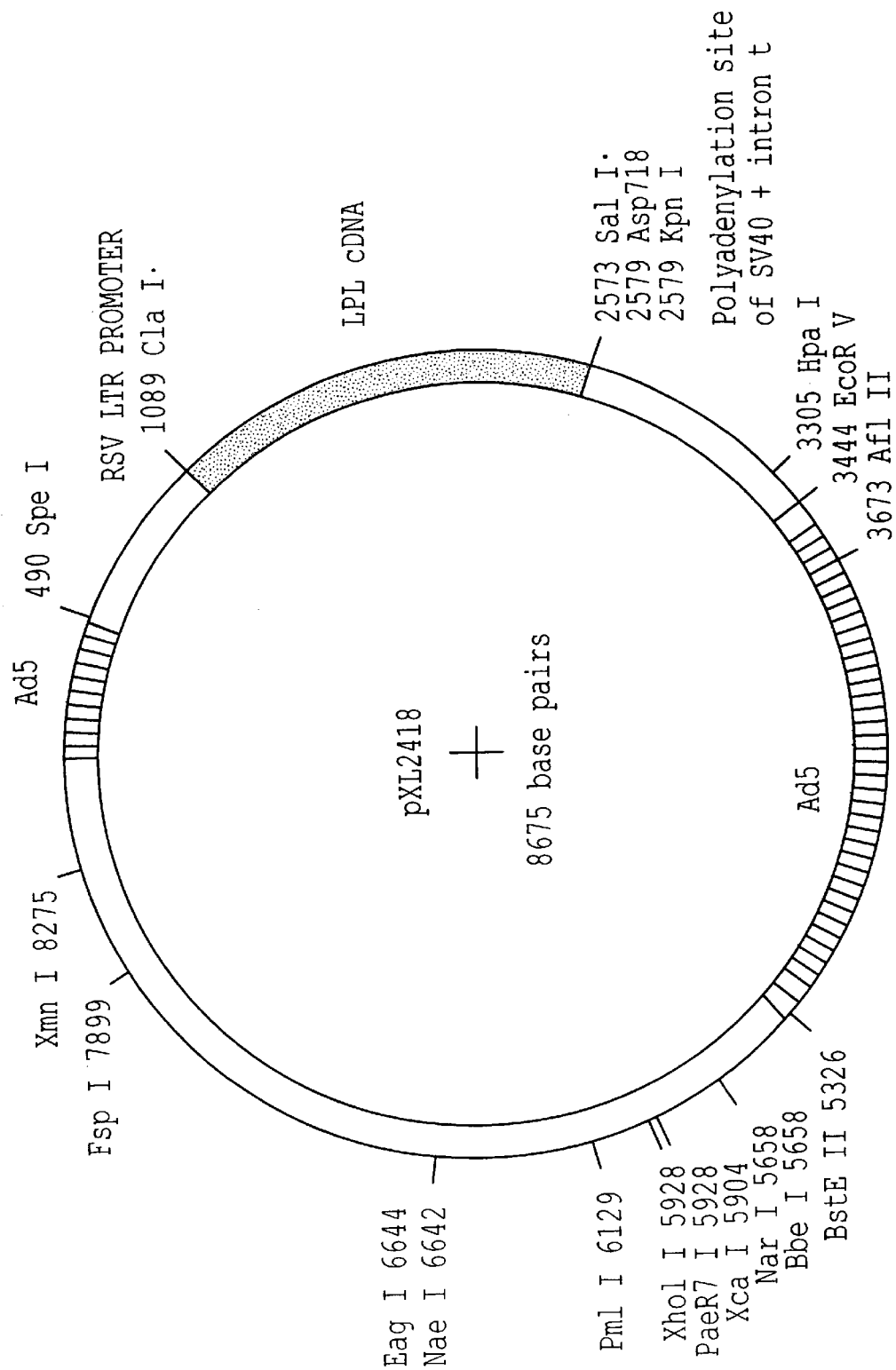
FIG. 2: Shows the structure of the vector pXL2419

Construction of the Vector pXL2419 Carrying the Gene Coding for LPL Under the Control of the Promoter of the Rous Sarcoma Virus LTR (RSV LTR) (FIG. 2)

This example describes the construction of a vector comprising a cDNA sequence coding for LPL, under the control of a promoter consisting of the Rous sarcoma virus LTR (RSV LTR), as well as a region of the Ad5 adenovirus genome permitting homologous recombination. This vector was constructed as described below.

2.1. Construction of the Vector pXL2244.

The vector pXL2244 contains, in particular, a region of the Ad5 adenovirus genome and a DNA sequence coding for apolipoprotein Al under the control of the RSV LTR promoter.

2.2. Construction of a cDNA Sequence Coding for LPL.

The cDNA sequence coding for LPL used in this example is that described in Example 1.2.

2.3. Construction of the vector pXL2419.

The LPL cDNA was inserted into plasmid pXL2244 between the SalI and ClaI sites, following excision of the Apo A1 cDNA with these same two enzymes. The plasmid obtained was designated pXL2419 (FIG. 2).

EXAMPLE 3

Construction of the Vectors pXL RSV-LPL and pXL CMV-LPL

Figure 3:
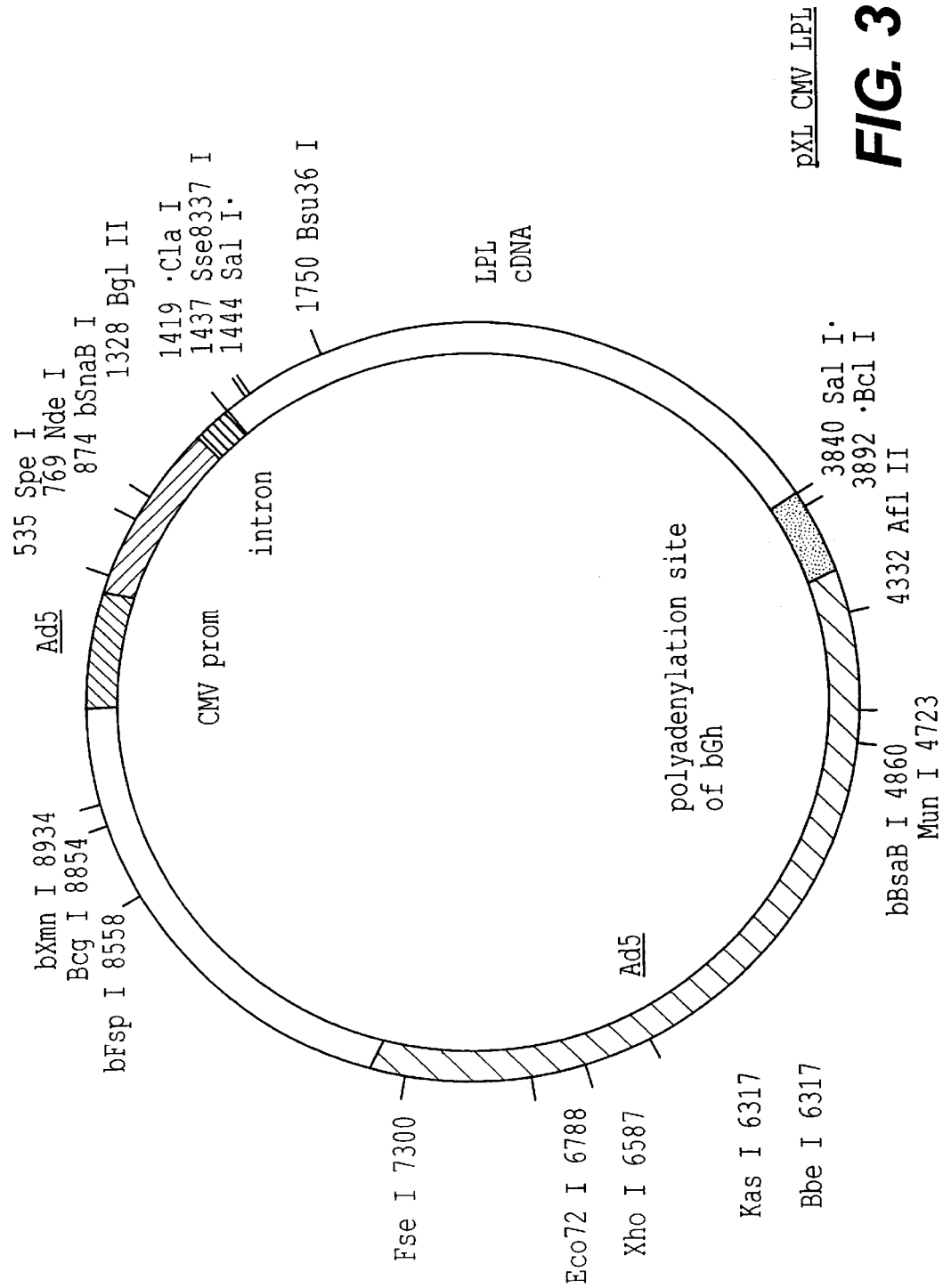
FIG. 3: Shows the structure of the vector pXL CMV-LPL
Figure 4:
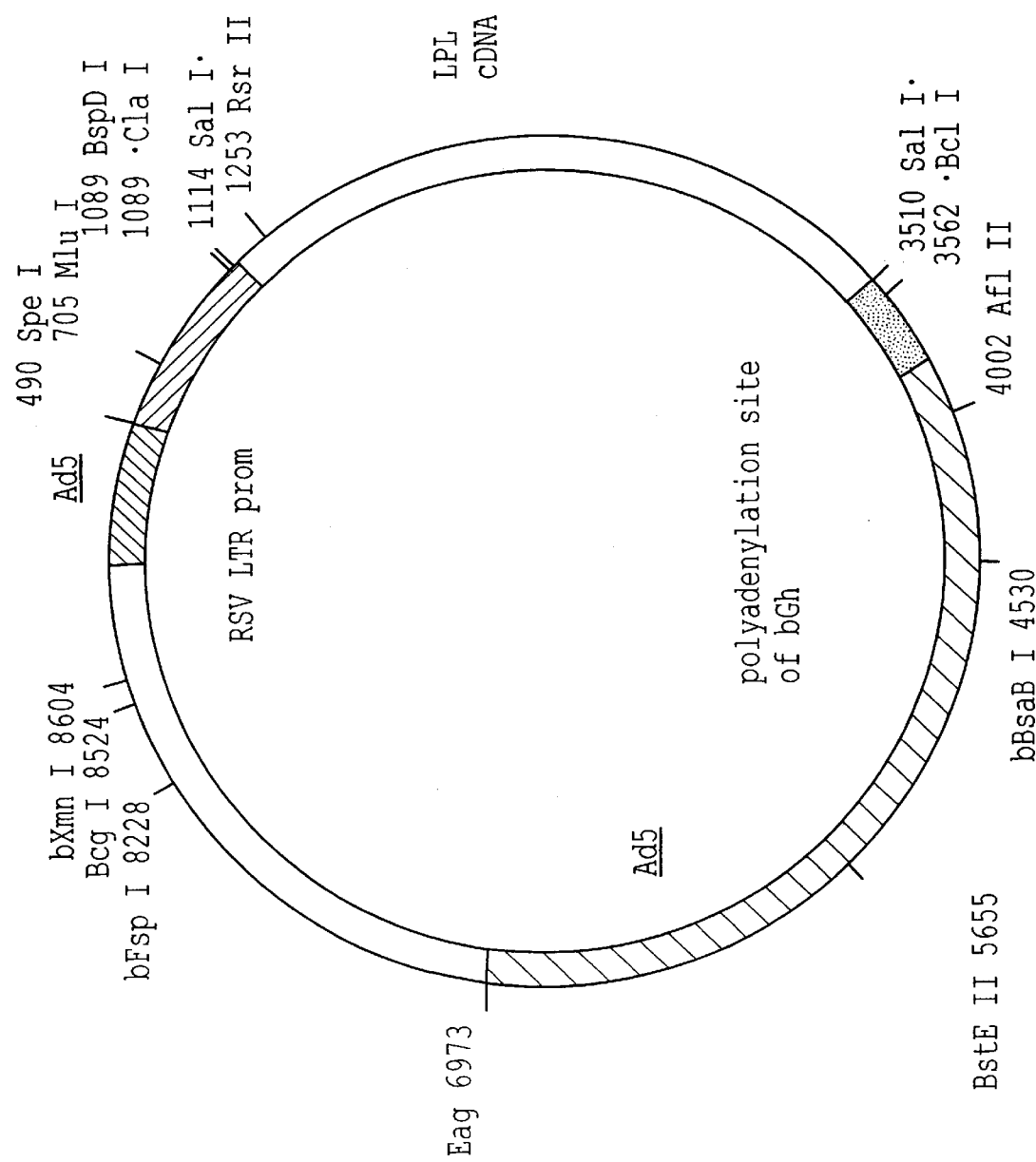
FIG. 4: Shows the structure of the vector pXL RSV-LPL

The vector pRC-CMV LPL contains a fragment of LPL cDNA extending from bases 1 to 2388 of the sequence published by Wion et al., cloned at the HindIII and XbaI sites of the expression vector pRC-CMV (Invitrogen). The HindIII site was modified to a ClaI site by inserting the oligonucleotide AGC TAC ATC GAT GT (SEQ ID NO: 3). The LPL cDNA and the polyadenylation site of bovine growth hormone (initially contained in pRC-CMV) are finally extracted from the pRCMV-LPL by SphI cleavage, treatment with T4 polymerase and ClaI cleavage. The fragment thereby obtained was cloned into the vectors pXL2418 (Example 1) and pXL2419 (Example 2) cut with ClaI and EcoRV, generating the vectors pXL CMV-LPL (FIG. 3) and pXL RSV-LPL (FIG. 4), respectively.

EXAMPLE 4

Construction of the Vector pXL RSV-LPLc

This example describes the construction of a vector which is usable to generate recombinant viruses containing a short cDNA coding for LPL.

A shorter cDNA (bases 146 to 1635 of the sequence of Wion et al.) was cloned from the RNA of human adipose tissue. The primers ATC GGA TCC ATC GAT GCA GCT CCT CCA GAG GGA CGC (SEQ ID NO: 4) and ATC TCT AGA GTC GAC ATG CCG TTC TTT GTT CTG TAG (SEQ ID NO: 5), which create, respectively, a BamHI site and a CalI site at the 5' end of the cDNA, as well as an XbaI site and a SalI site at the 3' end of the LPL cDNA, were used.

This PCR fragment was cloned into PCR II, and its sequence verified in its entirety. The LPL cDNA was then released via the BamHI and XbaI sites and cloned into an expression vector pcDNA3 (Invitrogen) for verification of the expression, generating plasmid pcDNA3-LPLc.

Figure 5:
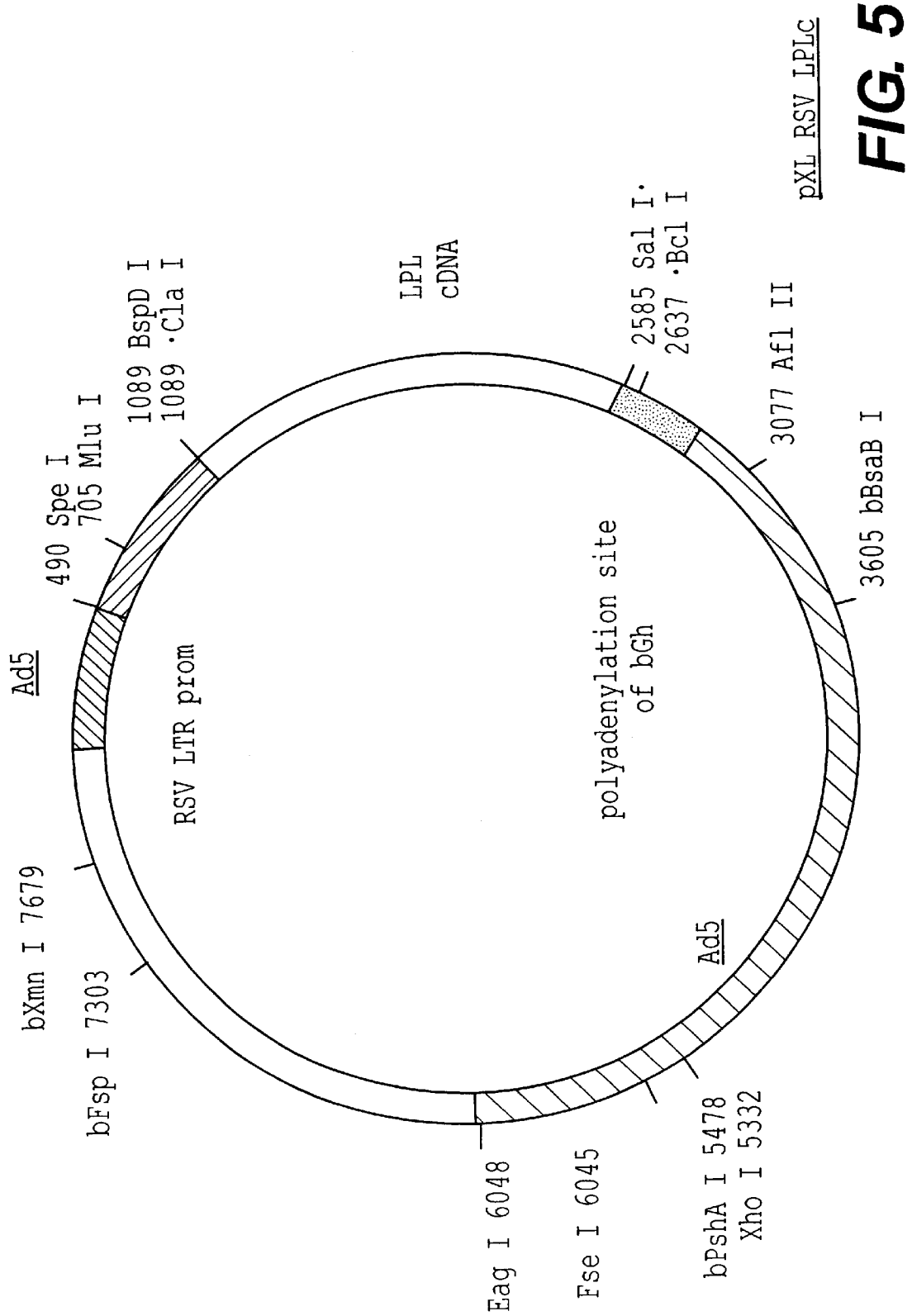
FIG. 5: Shows the structure of the vector pXL RSV-LPLc

The ClaI-SalI fragment containing the LPL cDNA was finally cloned at the same sites into plasmid pXL RSV-LPL (Example 3) to generate the shuttle plasmid pXL RSV-LPLc (FIG. 5).

EXAMPLE 5

Functionality of the Vectors of the Invention: Demonstration of an LPL Activity

The capacity of the vectors of the invention to express a biologically active form of LPL in a cell culture was demonstrated by transient transfection of 293 CosI cells. To this end, cells ($2 \times 10^6$ cells per dish 10 cm in diameter) were transfected (8µg of vector) in the presence of Transfectam. The expression of the sequence coding for LPL and production of a biologically active protein were demonstrated either in terms of mass using an immunoenzymatic test (5.1.), or in terms of lipase activity (5.2.).

5.1. Measurement of LPL in Terms of Mass.

An Immulon I ELISA plate (Dynatech) was coated with anti-bovine LPL monoclonal antibodies cross-reacting with human LPL (20 µg/ml in PBS, 50 µl/well). The potential sites remaining in the wells were then blocked (saturated) by incubation in the presence of I % gelatin for 1 hour at room temperature. The samples to be measured were then incubated for 1 hour at 37° C.

Visualization was carried out with an anti-LPL serum diluted to 10 µg/ml, 100 µl/well, followed by a peroxidase-labelled antiserum. Peroxidase activity was detected using a TMB substrate (Kirkegaard and Perry Laboratories Inc. kit) and reading of the absorbance at 490 nm.

5.2. Measurement of LPL Activity.

Total lipase activity was measured on a substrate composed of an emulsion of 0.3 mg of triolein (Sigma), 75 nCi of tri(1-$^{14}$C)oleoylglycerol (55 mCi/mmol, Amersham), 18 mg of BSA (Fraction V, Sigma) and 25 µl of normal human plasma as a source of ApoCII, all these constituents in a final volume of 500 µl of 0.223 M Tris pH 8.5. Generally speaking, activity was measured on 100 µl of supernatant of transfected cells or 50 µl of post-heparin plasma.

After 1 hour of incubation at 37° C., the reaction was stopped by adding 3.25 ml of extraction buffer (chloroform/methanol/heptane, 10:9:7 v/v/v) and 0.75 ml of carbonate/borate buffer pH 10.5, and the organic phase counted to determine the amount of fatty acids liberated.

To determine the activity specifically associated with LPL, the measurement of hepatic lipase activity was carried out in the presence of a I M concentration of NaCl (which inhibits LPL), and then subtracted from the total activity. It was also possible to inhibit lipoprotein lipase activity with a specific monoclonal antibody (Babirak et al., Atheriosclerosis, 1989, 9:326–334).

Plasmids pXL RSV-LPL and pXL CMV-LPL were tested by transfection into CosI cells by comparison with plasmid pRC CMV-LPL. The results are presented in Table 1.

TABLE 1

| Expression vector | Activity in the supernatant Day 1 |
|---|---|
| pRC-CMV-LPL | 24.5 |
| pXL RSV-LPL | 15.1 |
| pXL CMV-LPL | 22.9 |

Plasmid pcDNA-LPLc was tested by transfection into 293 cells by comparison with an expression vector pcDNA3 containing the same cDNA as the vector pRC-CMV-LPL. The results are presented in Table 2.

TABLE 2

| Expression vector | Activity in the supernatant Day 1 | Activity in the supernatant Day 2 |
|---|---|---|
| pCDNA3-LPL | 106.4 mU/ml | 106.7 mU/ml |
| pcDNA3-LPLc | 114 mU/ml | 109.6 mU/ml |

EXAMPLE 6

Construction of Recombinant Adenovirus Ad-CMV.LPL Containing a Sequence Coding for LPL Lipase The plasmids prepared in Examples 1 to 4 were linearized and cotransfected for recombination with the deficient adenoviral vector, in helper cells (line 293) providing in trans the functions encoded by the E1 (E1A and E11B) regions of adenovirus.

More especially, the adenovirus Ad.CMV.LPL was obtained by homologous recombination in vivo between the adenovirus Ad.RSVβgal (Stratford-Perricaudet et al., J. Clin. Invest 90 (1992) 626) and plasmid pXL2418 or pXL CMV-LPL according to the following protocol: the linearized plasmid pXL2418 or pXL CMV-LPL and the adenovirus labelled Ad.RSVµgal linearized with ClaI were cotransfected into line 293 in the presence of calcium phosphate to permit homologous recombination. The recombinant adenoviruses thus generated were selected by plaque purification. After isolation, the recombinant adenovirus was amplified in the cell line 293, yielding a culture supernatant containing the unpurified recombinant defective adenovirus having a titre of approximately $10^{10}$ pfu/ml.

The viral particles were then purified by centrifugation on a caesium chloride gradient according to known techniques (see, in particular, Graham et al., Virology 52 (1 973) 456). The adenovirus Ad-CMV.LPL were stored at −80° C. in 20 % glycerol.

The same protocol was reproduced with plasmid pXL2419 or pXL RSV-LPL or pXL RSV-LPLc, yielding the recombinant adenovirus Ad.RSV.LPL or Ad.RSV.LPLc.

EXAMPLE 7

In Vivo Transfer of the LPL Gene by a Recombinant Adenovirus

This example describes the transfer of the LPL gene in vivo by means of an adenoviral vector according to the invention.

The adenoviruses injected were the adenoviruses Ad-CMV.LPL and Ad.LTR.LPL prepared in Example 5, used in purified form ($3.5 \times 10^6$ pfU/µl), in saline phosphate solution (PBS). These viruses were injected into C57Bl/6 mice intravenously using the tail vein, the retro-orbital sinus or the portal vein. The expression of an active form of LPL was demonstrated under the conditions described in Example 5.

EXAMPLE 8

The significance of the mutation resulting in a serine in place of an asparagine as amino acid 291 in human lipoprotein lipase ("Asn291Ser mutation") was discovered as a result of a case controlled study of a large homogeneous sample of patients undergoing diagnostic coronary angiography. A total of 807 men, all of whom were of Dutch descent and had angiographically proven atherosclerosis with more than 50% stenosis of at least one major coronary vessel were included in the study. All of the patients were less than 70 years of age, and had total cholesterol levels between 4 and 8 mmol/l and triglyceride levels which did not exceed 4 mmol/l. The control group for the study included 157 persons who did not have any history of angina or premature atherosclerosis, and who exhibited no signs of vascular disease upon physical examination. The controls were all less than 60 years of age and had baseline HDL levels greater than 0.95 mmol/l and triglyceride levels of less than 2.3 mmol/l.

DNA was extracted from leukocytes using a salt-chloroform extraction method as described in Trends in Genetics 5: 391 (1989). Exon 6 of the LPL gene was amplified with a 5'-PCR primer located in intron 5 near the 5' boundary of exon 6 having the sequence

GCC GAG ATA C AA TCT TGG TG SEQ. ID. NO: 9 and a 3' mismatch primer which was located in exon 6 near the Asn291Ser mutation. The mismatch primer had the sequence

CTG CTT CTT T TG GCT CTG AC T GTA SEQ. ID. NO: 8

PCR amplification reactions were performed using 0.5 µg of genomic DNA in BRL PCR buffer containing 1.5 mM $MgCl_2$, 200 µM dNTPs, 1 µM each primer and 2.5 units Taq polymerase (BRL). The reaction mixture was denatured at 95° C. for 1 minute, annealed at 51° C. for 1 minute and extended at 72° C. for 45 seconds for a total of 35 cycles. Twenty µl of the PCR product was then digested with 10 units RsaI enzyme, 3,5 µl of 10× reaction buffer 1 (BRL), and 9.5 µl of water at 37° C. for 2 hours. The digested fragments were then separated on 2% agarose gel.

Because the combination of the mismatch primer and the Asn291Ser mutation produces an RsaI restriction site which is absent when the mismatch primer is used to amplify the wild-type gene, the restriction fragments observed on the agarose gel were different when the mutation was present. Using this difference as a diagnostic indicator, it was determined that the Asn291Ser mutation was seen in 41 of the 807 or 5.09% of the patients in the test group, but in only 3 out of 157 or 1.9% of the patients in the control group. When a subgroup of the 494 patients in the test group with hypoalphalipoproteinemia was considered, it was found that a higher percentage of these patients, i.e., 6.9 % (34 out of 494) had the Asn291Ser mutation. When a further subgroup of the test group was considered by selecting those individuals with low HDL-C levels (<1.0%), and excluding those individuals who had blood glucose >6.8 mmol/l (suggestive of diabetes) and those on β-blocker therapy, 11.3% (12 out of 106 patients) had the mutation. This proportion further increased when those with still lower HDL-C levels were considered separately. Thus, among persons with HDL-C levels less than 0.9 mmol/l, 8 out of 68 or 12.5 % had the Asn291Ser mutation, while among those with HDL-C levels less than 0.8 mmol/l, 5 out of 32 or 15.6% had the Asn291Ser mutation.

EXAMPLE 9 pRc/CMV vector (Invitrogen) was linearized using XbaI and Hind III. An XbaI/HindIII fragment containing h-LPL cDNA having a length of about 2.4 kb was inserted into the vector. DH5-alpha was transformed with the construct. Transformed cells were selected from agar plates based upon ampicillin resistance, and grown in LB medium. The plasmid construct, pRc/CMV-hLPL which is shown in FIG. 9, was isolated from the cultures by alkaline lysis and CsCl centrifugation.

EXAMPLE 10

A purified preparation of an incompetent adenovirus (E1A deletion mutant) was prepared by growing 293 cells in 2 liter spinner flasks to a cell density of 4.5 $\times 10^6$/ml and infecting the cells with DL312 adenovirus stock at MOI (multiplicity of infection) 20–50 for 1 hour. Forty hours post infection, the cells were harvested by centrifugation. A lysate was prepared by subjecting the harvested cells to 3 freeze/thaw cycles. This lysate was centrifuged in a two-layer CsCl gradient (d=1.25, d=1.4)in a Beckman SW41 swing rotor at 35,000 rpm and 18° C. for 90 minutes. After the ultracentrifugation, the virus was recovered from the interface between the two CsCl layers using a syringe and a long needle. The recovered virus was then placed onto a CsCl solution (d=1.34) and centrifuged for 16 hours at 35,000 rpm and 18° C. After this centrifugation, the virus was again recovered from the interface and was then dialyzed three times (1 hour per cycle) against a sterile buffer (Tris 10 mM, $MgCl_2$ 1 mM, NaCl 0.135 M). In the third dialysis cycle, the buffer included 10% glycerol to enhance storage stability. The purified virus was kept frozen at −80° C. until ready to use.

EXAMPLE 11

Virus prepared as described in Example 10 was mixed with polylysine (10 mM) and EDC (2 mM) for 4 hours at 4° C. in HBS/buffered saline to form adenovirus-polylysine conjugates. The conjugates were re-isolated by CsCl gradient centrifugation using the same protocol as the final centrifugation in Example 3.

The re-isolated conjugates ($5 \times 10^9$/ml) were incubated with 60–70% confluent Chinese Hamster Ovary cells (CHO K-1) in 2% FBS medium (1 ml) and 6 µg of the plasmid pRc/ CMV-hLPL. As a control to assess the extent to which transfection occurred, a second set of samples was prepared in the same manner using the plasmid pRc/CMV-B-gal which includes a gene encoding β-galactosidase in place of h-LPL. After two hours, the medium containing the conjugates was aspirated out, and new medium (10% FBS) was added to the cells.

By incubating the control cells infected with pRc/CMV-B-gal in the presence of X-gal, and counting the number of cells which evidenced the characteristic blue color which result from cleavage of X-gal by β-galactosidase, it was determined that the transfection efficiency in this system varied from 2% when the virus solution was diluted 2000×to 50% when the virus solution was diluted 125×. Thus, 50 % transfection efficiency could be achieved in vitro at titers of $0.5 - 1 \times 10^8$, which is at least 10-fold less than the titers which would normally be used in vivo.

To determine the expression of LPL in cells transfected with pRc/CMV-LPL, the activity of LPL was determined and compared to the activity observed for control cells transfected with pRc/CMV-B-gal. For the control cells, the activity measured was 12 mU/ml. For the cells transfected with pRc/CMV-LPL, the activity measured was 20 mU/ml.

EXAMPLE 12

The experiments described in Example 11 were repeated, except that the cells used were LPL-deficient cat fibroblast cells or HepG-2 liver cells. Table 3 shows the infection efficiencies at various virus dilutions which were determined for these cell types as well as the CHO K-1 cells.

TABLE 3

| | DILUTION | | | | |
|---|---|---|---|---|---|
| VIRUS | 2000× | 1000× | 500× | 250× | 125× |
| CHO K-1 | 2 | 5 | 15 | 30 | 50 |
| Cat Fibroblast | 10 | 20 | 50 | 100 | 100 |
| HepG-2 | 20 | 50 | 100 | 100 | 100 |

Table 4 shows the LPL activity measured for Cat fibroblast cells, and the LPL mass measured for cat fibroblast cells and HepG-2 cells. In addition, Table 4 shows positive control results for COS EV 101 cells which are over producers of LPL. It can be seen from this data that there is a substantial increase in the plasmid activity and also in the amount of the active dimer form of the enzyme.

TABLE 4

| | | LPL Activity | LPL MASS (ng/ml) | | |
|---|---|---|---|---|---|
| Cell Type | plasmid | (mU/ml) | total | monomer | dimer |
| CHO K-1 | control | 12 | n.d. | n.d. | n.d. |
| | pRc/CMV-LPL | 20 | n.d. | n.d. | n.d. |
| Cat Fibroblasts | control | 0.15 | 26 | 24 | 2 |
| | pRc/CMV-LPL | 1.5 | 128 | 88 | 34 |
| HepG-2 | control | n.d. | 33 | 28 | 6 |
| | pRc/CMV-LPL | n.d. | 164 | 113 | 51.5 |
| COS | EV101 | 50 | 530 | 87 | 443 |

EXAMPLE 13

Vectors for introducing human LDL cDNA into mammalian cells were made using the murine leukemia retroviral backbones M3neo, M5neo and JZen1 which contain long terminal repeat (LTR) regulatory sequences for the myeloproliferative sarcoma virus. To generate the vectors M3neoLPL and M5neoLPL, a 1.56 kb DraI-EcoRI fragment encompassing the entire LPL amino acid coding region was subcloned into a unique BamHI site located 3' or 5' to the neomycin phosphotransferase ($neo^r$), respectively. Expression of both genes is LTR driven in these vectors; in M3neoLPL, functional LPL message would derive from the spliced proviral transcripts whereas for M5neoLPL, LPL message would derive from the full length unspliced proviral transcript. To construct JZenLPLtkneo, a 1092 bp Xho I/SalI fragment for $neo^r$ was isolated from pMCIneo and inserted into the SalI site of the plasmid pTZ 19R, containing the herpes simplex virus thymidine kinase (tk) promoter. The SmaI/HindIII tkneo fragment from the pTZ19R was inserted into the Hpa I/Hind III site of JZen1. A 1.56 kb human LPL cDNA sub-fragment was then cloned in the BamHI site of JZentkneo. Human LPL cDNA was also subcloned directly into JZen1 to construct JZenLPL.

Virus producer cells lines were then made for each of the viral constructs using the amphotropic retroviral packaging cell line GP-Am 12 and the ecotropic packaging line GP-E86. Both cell lines were cultured in HXM medium, which is Dulbecco's modified Eagle's medium (DME) supplemented with 10% heat-inactivated (55° C. for 20 minutes) newborn calf serum (Gibco-BRL), hypoxanthine (15 µg/ml), xanthine (250 µg/ml) and mycophenolic acid (25 µg/ml). For GP-AM12 cells, hygromycin B (200 µg/ml) was also added to the HXM medium. All cells were cultured at 37° C. in a humidified atmosphere of 5% $CO_2$.

EXAMPLE 14

A variety of hematopoietic cell lines were tested using the neomycin resistance marker incorporated in the vector to determine whether transduction occurred as a result of coincubation with M3neoLPL in vitro. K562 erythroid cells, HL60 myeloid cells, and U937 and THP-1 monocytic cells obtained from the American Type Culture Collection were grown in RPMI 1640 medium containing 10% fetal bovine serum. The cells were then infected by cocultivation (24–48 hours) with irradiated (15 Gy x-ray) near confluent producer cells with polybrene 4 µg/ml added to the co-cultivation medium (RPMI/ 10% fetal bovine serum). After the infection period, the hematopoietic target cells were maintained in suspension culture for 24 hours before selection in 1 mg/ml G418. The gene transfer efficiencies observed are summarized in Table 5.

The mass of LPL produced was determined for each of the transduced hematopoietic cells lines using two ELISAs. The antibodies used were MAb 5D2 which binds to the bioactive dimeric form of LPL and MAb 5F9 which binds to both the bioactive dimer and the inactive monomeric form of LPL. The results are summarized in Table 5. Finally media supernatants were measured for LPL bioactivity. The results of this study are also reported in Table 5.

TABLE 5

| Cell Line | Gene Transfer Efficiency | Increase in Bioactivity | Increase in LPL Dimer |
|---|---|---|---|
| K562 | 57% | 11-fold | 5-fold |
| HL60 | 47% | 9-fold | 3-fold |
| U937 | 45% | 14-fold | 54-fold |
| THP-1 | 41% | 4-fold | 2-fold |

These results demonstrate that for each cell type, good transduction efficiencies were achieved, and production of functional LPL resulted.

Transduced HL60 and THP-01 cells were differentiated in macrophages by exposing the cells to 10ng/ml of phorbal ester, PdBU (Phorbol 12,1 3-dibutyrate) for 5 days. For HL60 cells, the LPL bioactivity increased a further 1.8-fold, while the amount of LPL dimer increased another 1.8-fold. No further increase was observed 5 upon differentiation of THP-1 cells.

EXAMPLE 15

NIH 3T3 murine fibroblasts were grown in DME medium containing 10% (vol/vol) fetal bovine serum. The medium on near confluent 60 mm tissue culture plates of viral producer cells 24 hours prior to the planned infection with 10 ml DME/10% newborn calf serum. This medium was removed at the time of infection, concentrated 10-fold to a 1.0 ml final volume by filter centrifugation in Centriprep- 30 tubes (Amicon) and diluted 1:4 with DME/10% fetal bovine serum with 4 µg/ml polybrene added. Fibroblasts were added to this preparation and incubated for 24–48 hours at 37° C. 24 hours after viral exposure, cells were subjected to selection in 1.0 mg/ml G418 and grown to confluence. Testing for LPL production revealed a 16-fold increase in total LPL production above constitutive levels which consisted almost entirely of dimeric protein, and a 10-fold increase in secreted LPL bioactivity.

EXAMPLE 16

The experiment of Example 15 was repeated using primary human fibroblast cells, FC 1898 and FC 1901 from diagnostic skin biopsies. No measurable levels of endogenous LPL protein mass or bioactivity could be detected prior to retroviral-mediated LPL gene delivery. Post transduction levels of total LPL mass were massively elevated at least 400 times above normal. However, at least 82% of this exogenous LPL protein was of the inactive monomeric form. At least a 52-fold (74.8±22/9) increase in dimeric LPL production was seen with significantly elevated secretion of bioactive LPL, approximately 24 times higher (26.9±3.0) than background LPL levels.

---

We claim:

1. A method for treating a patient with dyslipoproteinaemia comprising administering to the patient via intravenous injection a defective recombinant adenovirus comprising a nucleic acid sequence coding for a biologically active human lipoprotein lipase (LPL), wherein the nucleic acid sequence is operably linked to a promoter, and wherein the nucleic acid sequence is expressed so as to cause a reduction of lipoprotein in the patient.

2. A method for treating a patient with hypertriglyceridaemia comprising administering to the patient via intravenous injection a defective recombinant adenovirus comprising a nucleic acid sequence coding for a biologically active human lipoprotein lipase (LPL) wherein the nucleic acid sequence is operably linked to a promoter, and wherein the nucleic acid sequence is expressed so as to cause a reduction of triglyceride in the patient.

3. A method for treating a patient with hypercholesterolaemia comprising administering to the patient via intravenous injection a defective recombinant adenovirus comprising a nucleic acid sequence coding for a biologically active human lipoprotein lipase (LPL), wherein the nucleic acid sequence is operably linked to a promoter, and wherein the nucleic acid sequence is expressed so as to cause a reduction of cholesterol in the patient.

4. A method for treating a patient with hyperlipidaemia comprising administering to the patient via intravenous injection a defective recombinant adenovirus comprising a nucleic acid sequence coding for a biologically active human lipoprotein lipase (LPL), wherein the nucleic acid sequence is operably linked to a promoter, and wherein the nucleic acid sequence is expressed so as to cause a reduction of lipid in the patient.

5. A method for treating a patient with familial hypertriglyceridaemia comprising administering to the patient via intravenous injection a defective recombinant adenovirus comprising a nucleic acid sequence coding for a biologically active human lipoprotein lipase (LPL) wherein the nucleic acid sequence is operably linked to a promoter, and wherein the nucleic acid sequence is expressed so as to cause a reduction of triglyceride in the patient.

6. A method for treating a patient with combined familial hyperlipidaemia and postprandial hyperlipidaemia comprising administering to the patient via intravenous injection a defective recombinant adenovirus comprising a nucleic acid sequence coding for a biologically active human lipoprotein lipase (LPL), wherein the nucleic acid sequence is operably linked to a promoter, and wherein the nucleic acid sequence is expressed so as to cause a reduction of lipid in the patient.

7. The method of treatment according to claim 1, wherein the defective recombinant adenovirus is administered by direct injection into the patient's portal vein, such that viral infection is targeted to the liver.

8. The method according to one of claims 1–6, wherein the defective recombinant adenovirus is selected from the group consisting of human adenovirus type Ad 2, human adenovirus type Ad 5, and canine adenovirus type CAV-2.

9. The method according to one of claims 1–6, wherein the promoter is a viral promoter.

10. The method according to claim 9, wherein the viral promoter is selected from the group consisting of an E1A promoter, a MLP promoter, a CMV promoter, and a RSV LTR promoter.

11. The method according to claim 9, wherein the viral promoter is the RSV LTR promoter.

12. The method according to claim 7, wherein the defective recombinant adenovirus is selected from the group consisting of human adenovirus type Ad 2, human adenovirus type Ad 5, and canine adenovirus type CAV-2.

13. The method according to claim 7, wherein the promoter is a viral promoter.

14. The method according to claim 7, wherein the viral promoter is selected from the group consisting of an E1A promoter, a MLP promoter, a CMV promoter, and a RSV LTR promoter.

15. The method according to claim 7, wherein the viral promoter is the RSV LTR promoter.

* * * * *